United States Patent
Chi et al.

(10) Patent No.: US 11,753,378 B2
(45) Date of Patent: Sep. 12, 2023

(54) KETAMINE COMPOUNDS AND PROCESSES FOR MAKING AND USING THEM

(71) Applicant: Zevra Therapeutics, Inc., Celebration, FL (US)

(72) Inventors: Guochen Chi, Coralville, IA (US); Sven Guenther, Coralville, IA (US); Travis Mickle, Kissimmee, FL (US); Adam Smith, Orlando, FL (US)

(73) Assignee: Zevra Therapeutics, Inc., Celebration, FL (US)

( * ) Notice: Subject to any disclaimer, the term of this patent is extended or adjusted under 35 U.S.C. 154(b) by 0 days.

(21) Appl. No.: 17/723,189

(22) Filed: Apr. 18, 2022

(65) Prior Publication Data
US 2022/0348544 A1    Nov. 3, 2022

Related U.S. Application Data

(60) Provisional application No. 63/176,499, filed on Apr. 19, 2021.

(51) Int. Cl.
*C07D 213/79* (2006.01)
*C07D 401/12* (2006.01)
*C07F 9/10* (2006.01)
*C07D 265/30* (2006.01)
*C07D 213/80* (2006.01)

(52) U.S. Cl.
CPC ......... *C07D 213/79* (2013.01); *C07D 213/80* (2013.01); *C07D 265/30* (2013.01); *C07D 401/12* (2013.01); *C07F 9/10* (2013.01)

(58) Field of Classification Search
CPC .. C07D 213/79; C07D 213/80; C07D 265/30; C07D 401/12; C07F 9/10
See application file for complete search history.

(56) References Cited

U.S. PATENT DOCUMENTS

2004/0248964 A1    12/2004    Crooks et al.
2020/0231540 A1    7/2020    Xiang et al.

FOREIGN PATENT DOCUMENTS

WO    2007038949    4/2007
WO    2019137381    * 7/2019

OTHER PUBLICATIONS

PCT, International Search Report regarding Application No. PCT IUS2022/025266, 17 pages, dated Aug. 17, 2022.

* cited by examiner

*Primary Examiner* — D Margaret M Seaman
(74) *Attorney, Agent, or Firm* — McAndrews, Held & Malloy, Ltd.

(57) ABSTRACT

Disclosed are compounds comprising ketamine (2-(2-chlorophenyl)-2-(methylamino)-cyclohexanone) chemically conjugated to one or more oxoacids, amino acids, polyethylene glycols (PEG or PEO), peptides, phosphates, and/or vitamin compounds, and salts of such compounds. Also disclosed are compositions comprising at least one ketamine compound, or a salt thereof, methods of making such compounds, and methods of using such ketamine compounds and compositions.

33 Claims, 22 Drawing Sheets

Ketamine

Norketamine

KETAMINE COMPOUNDS AND PROCESSES FOR MAKING AND USING THEM

RELATED APPLICATIONS

The present patent application claims the priority benefit of U.S. Provisional Patent Application Ser. No. 63/176,499, filed Apr. 19, 2021, the content of which is hereby incorporated by reference in its entirety into this disclosure.

BACKGROUND

Ketamine (2-(2-chlorophenyl)-2-(methylamino)-cyclohexanone) is a long-known anesthetic agent first synthesized in the early 1960s as a safer alternative to phencyclidine (PCP). It exists as two stereo-isomeric forms: S(+) and R(−). The S(+) isomer is the most potent NMDA receptor antagonist known and is approximately three to four times that of the R(−) isomer. Ketamine is used clinically as a racemic mixture containing equal amounts of both isomers. More recently, drug products have isolated the more potent S(+) isomer of ketamine. Although ketamine has largely fallen out of favor as a general anesthetic due to newer drugs, its clinical use has surged since off-label uses have been reported.

Off-label uses of ketamine have included treating chronic pain, acute pain, neuropathic pain, cancer pain, complex regional pain syndrome (CRPS), fibromyalgia, depression, post-traumatic stress disorder (PTSD), suicidal ideation, and other pain, psychiatric, or autoimmune disorders. Perhaps the most promising is the discovery that ketamine can rapidly treat major depressive disorders. Depression is notoriously difficult to treat for many reasons. First-line therapies often include selective serotonin reuptake inhibitors (SSRIs). These drugs are associated with serious side effects and often necessitate weeks of daily dosing before anti-depressive effects are observed. In the case of severe depression and comorbid suicidal ideation, a patient may not have weeks to wait for relief, and many take their life before the medications can take effect. As such, ketamine represents a significant advancement toward the goal of developing a fast-acting anti-depressant with the potential to also reduce suicidal ideations.

Recently, the first ketamine product (Spravato) was approved for Treatment-Resistant Depression and Major Depressive Disorder with suicidal ideation. Spravato uses the S-enantiomer of ketamine (esketamine) and is delivered via a nasal spray. The drug can only be administered in the clinical setting, and physicians are required to monitor the patient for at least 2 hours following administration. In addition, the pharmacokinetic profile following an intranasal dose of Spravato is quite aggressive, such that there is a rapid spike of ketamine detectable in blood, followed by a rapid elimination phase. This pharmacokinetic profile may contribute to the drug's adverse event profile, which includes hypertension, feeling disconnected from yourself, dizziness, nausea, anxiety, etc. It is currently unknown if such a pharmacokinetic profile is needed to achieve the desired therapeutic effect. However, experiences from clinical practice and published literature suggest that sustained sub-anesthetic plasma levels of ketamine produce the desired therapeutic effect without such adverse events.

At present, most clinical practices that offer ketamine treatment for off-label indications administer the drug intravenously. While there could be many reasons for this, certainly one reason is that when ketamine is administered orally, it undergoes significant pre-systemic metabolism that reduces efficacy. Intravenous administration provides complete bioavailability but is a less desirable route of administration since it necessitates an outpatient visit to the clinic where patients undergo infusion sessions that generally last for more than an hour (4 hours is common). Moreover, standard IV protocols also require multiple days of infusion to see a significant, sustained effect.

Unfortunately, ketamine is also a known drug of abuse. Abusers seek a rapid high and achieve this by snorting ketamine powder (most common) or by injecting ketamine intravenously (less common). Long-term ketamine abuse is associated with bladder and kidney damage that has not yet been observed with typical therapeutic uses of ketamine. That ketamine is a known drug of abuse presents a significant challenge for developing a commercial, take-home, prescription ketamine drug product.

BRIEF SUMMARY

The present technology provides compounds of the ketamine, salts of such compounds, and combinations thereof. The present technology utilizes conjugation of ketamine with certain nicotinic acids, isonicotinic acids, pyridines, morpholines, phosphates, oxoacids, amino acids, and/or peptides, or derivatives thereof. Following administration in a human or animal subject, ketamine is released through enzymatic or metabolic breakdown of the conjugate in vivo. The present technology also provides compositions comprising the ketamine compounds, and methods of delivering the ketamine compounds as conjugates that release the ketamine following oral administration while being resistant to abuse by circuitous routes such as intravenous ("shooting") injection and intranasal administration ("snorting"). In addition, the present technology provides compositions comprising the ketamine compounds, and methods of delivering the ketamine compounds as conjugates that improve oral bioavailability of unconjugated ketamine, and/or decrease the formation of the norketamine metabolite.

In some aspects, the present technology provides ketamine compound, or salt of the compounds comprising ketamine, and at least one nicotinic acid, isonicotinic acid, pyridine, morpholine, phosphate, oxoacid, amino acid, and/or peptide, or derivatives thereof. In some aspects, the ketamine compounds further comprise a linker, wherein the linker chemically bonds at least one ketamine molecule with at least one nicotinic acid, isonicotinic acid, pyridine, morpholine, phosphate, oxoacid, amino acid, and/or peptide, or derivatives thereof.

In a further aspect, the present technology provides a ketamine compound comprising ketamine, wherein the ketamine compound has the following general Formula I:

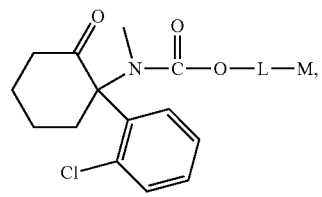

Formula I where L is selected from alkyl, alkenyl, alkynyl, alkoxy, alkylamino, aryl, substituted aryl, and cycloalkyl;

where M is selected from

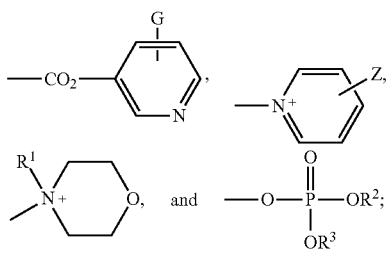

where G is selected from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, and thiol;

where Z is selected from hydrogen,

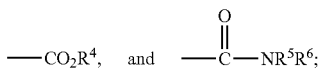

and where $R^1$, $R^2$, $R^3$, $R^4$, $R^5$, and $R^6$ are independently selected from hydrogen, alkyl, alkenyl, alkynyl, alkoxy, alkylamino, aryl, substituted aryl, and cycloalkyl.

When M is

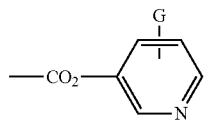

the ketamine compound may have the following Formula II:

Formula II

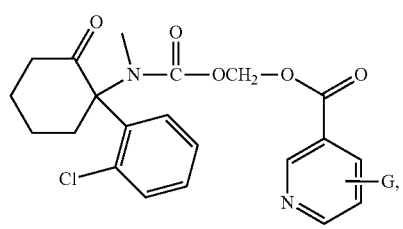

where G has the same meaning above.

When M is

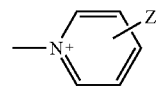

the ketamine compound may have the following Formula III:

Formula III

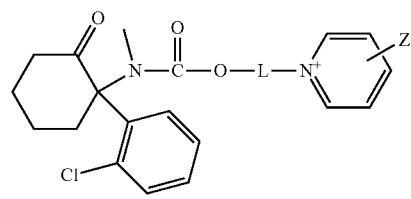

where Z has the same meaning above.

When M is

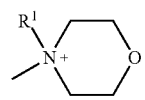

the ketamine compound may have the following Formula IV:

Formula IV

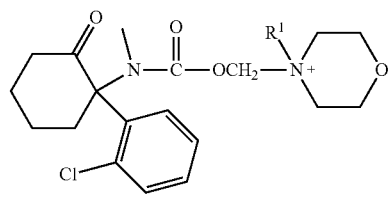

where $R^1$ has the same meaning above.

When M is

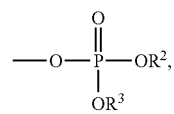

the ketamine compound may have the following Formula V

Formula V

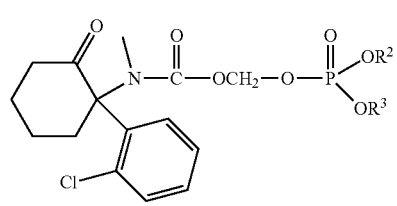

where $R^2$ and $R^3$ have the same meaning above.

In another aspect, the present technology provides at least one composition comprising at least one ketamine compound or salt of the compound, the ketamine compound or salt of the compound comprising ketamine, derivatives thereof or combinations thereof, and at least one nicotinic acid, isonicotinic acid, pyridine, morpholine, phosphate, oxoacid, amino acid, and/or peptide, or derivatives thereof.

In another aspect, the present technology provides at least one composition comprising at least one ketamine compound, wherein the at least one compound can be, for example, ketamine-$CO_2CH_2$-nicotinoyl-sarcosine, ketamine-$CO_2CH_2$-nicotinoyl-glycine, ketamine-$CO_2CH_2$-nicotinoyl-alanine, ketamine-$CO_2CH_2$-nicotinoyl-valine, ketamine-$CO_2CH_2$-nicotinoyl-isoleucine, ketamine-$CO_2CH_2$-nicotinoyl-proline, ketamine-$CO_2CH_2$-nicotinoyl-lysine, ketamine-$CO_2CH_2$-nicotinoyl-hydroxyproline, ketamine-$CO_2CH_2$-nicotinoyl-tyrosine, ketamine-$CO_2CH_2$-nicotinoyl-phenylalanine, ketamine-$CO_2CH_2$-nicotinoyl-glutamine, ketamine-$CO_2CH_2$-nicotinoyl-asparagine, ketamine-$CO_2CH_2$-nicotinoyl-aspartic acid, ketamine-$CO_2CH_2$-nicotinoyl-glutamic acid, ketamine-$CO_2CH_2$-nicotinoyl-ornithine, ketamine-$CO_2CH_2$-nicotinoyl-serine, ketamine-$CO_2CH_2$-nicotinoyl-threonine, ketamine-$CO_2CH_2$-isonicotinoyl-ornithine, ketamine-$CO_2CH_2$-nicotinoyl-leucine, ketamine-$CO_2CH_2$-nicotinoyl-methionine, ketamine-$CO_2CH_2$-3-(3-pyridyl)alanine, ketamine-$CO_2CH_2$-nicotinoyl-arginine, ketamine-$CO_2CH_2$-nicotinoyl-morpholine, ketamine-$CO_2CH_2$-niacin, ketamine-$CO_2CH_2$-nicotinate(tBu), ketamine-$CO_2CH_2$-nicotinate (Et), ketamine-$CO_2CH_2$-nicotinate(Me), ketamine-$CO_2CH_2$-nicotinamide, ketamine-$CO_2CH_2$-nicotinamide (N-MeO, N-Me), ketamine-$CO_2CH_2$-nicotinamide(methyl pipecolinate), ketamine-$CO_2CH_2$-nicotinamide(di-Me), ketamine-$CO_2CH_2$-nicotinamide(N-BzO, N-Me), Phosphate-$CH_2OC(O)$-ketamine, Nicotinate-$CH_2OC(O)$-ketamine, Isonicotinate-$CH_2OC(O)$-ketamine, ketamine-$CO_2CH_2$-nicotinoyl-sarcosine ethyl ester, ketamine-$CO_2CH(CH_3)$-nicotinoyl-proline, ketamine-$CO_2CH(CH_3)$-nicotinoyl-sarcosine, ketamine-$CO_2CH_2$-isonicotinoyl-sarcosine, ketamine-$CO_2CH_2$-nicotinoyl-N-Me-alanine, ketamine-$CO_2CH_2$-isonicotinoyl-N-Me-alanine, ketamine-$CO_2CH_2$—N-Me-morpholine, ketamine-$CO_2CH_2$—N-Me-diethanolamine, ketamine-$CO_2CH_2$-nicotinoyl-3-aminobenzoic acid, ketamine-$CO_2CH_2$-isonicotinoyl-3-aminobenzoic acid, ketamine-$CO_2CH_2$-isonicotinate(tBu), ketamine-$CO_2CH_2$-isonicotinic acid, ketamine-$CO_2CH_2$-nicotinoyl-glycine ethyl ester, ketamine-$CO_2CH_2$-nicotinoyl-L-2-aminobutyric acid, ketamine-$CO_2CH_2$-nicotinoyl-Gly-Gly, ketamine-$CO_2CH_2$-nicotinoyl-Gly-Ala, ketamine-$CO_2CH_2$-isonicotinoyl-Gly-Ala, ketamine-$CO_2CH_2$-nicotinoyl-Phe-Phe, ketamine-$CO_2CH_2$-isonicotinoyl-Phe-Phe, ketamine-$CO_2CH_2$-nicotinoyl-Phe-Phe-Phe, S-KTM-$CO_2CH_2$-nicotinoyl-sarcosine ethyl ester, S-KTM-$CO_2CH_2$-nicotinoyl-valine, Isonicotinate-$CH_2OC(O)$—(S)-KTM, S-KTM-$CO_2CH_2$-nicotinoyl-ornithine, S-KTM-$CO_2CH_2$-3-(3-pyridyl)alanine, S-KTM-$CO_2CH_2$-niacin, R-KTM-$CO_2CH_2$-nicotinoyl-ornithine, Isonicotinate-$CH_2OC(O)$—(R)-KTM, R-KTM-$CO_2CH_2$-3-(3-pyridyl) alanine, R-KTM-$CO_2CH_2$-niacin, R-KTM-$CO_2CH_2$-nicotinoyl-valine, R-KTM-$CO_2CH_2$-nicotinoyl-sarcosine ethyl ester, and anionic salts thereof, including hydrochloride/chloride salts. In another aspect, the composition may further comprise one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

In another aspect, the composition is in a form selected from the group consisting of a liquid, a sublingual, a gummy, a chewable tablet, a rapidly dissolving tablet, a tablet, a capsule, a caplet, a troche, a lozenge, an oral powder, a solution, a thin strip, an oral thin film (OTF), an oral strip, a rectal film, a syrup, a suspension, or a suppository. In yet another aspect, the composition has a dosing regimen that is about two times a day or less, alternatively about one time a day. In another aspect, the composition is administered orally, intranaslly, or intravenously to a subject in need thereof. In an aspect, the subject is a human or animal subject.

In another aspect, the present technology provides for an oral formulation comprising a therapeutically effective dose of a claimed ketamine compound. In some aspects, the oral formulation is in the form selected from the group consisting of a liquid, a sublingual, a gummy, a chewable tablet, a rapidly dissolving tablet, a tablet, a capsule, a caplet, a troche, a lozenge, an oral powder, a solution, a thin strip, an oral thin film (OTF), an oral strip, a syrup, or a suspension. In some aspects, the oral formulation has a dosing regimen that is about two times a day or less, alternatively about one time a day.

In another aspect, the present technology provides a pharmaceutical kit comprising a specified amount of individual doses in a package, wherein each individual dose comprises a therapeutically effective amount of a composition comprising any of the ketamine compounds.

In yet another aspect, the present technology provides a method for chemically synthesizing any of the ketamine compounds of the present technology by performing the appropriate steps to conjugate ketamine to at least one ligand.

In yet another aspect, the present technology provides methods for increasing oral bioavability, reducing norketamine exposure, reducing intranasal bioavability, reducing intravenous bioavailability, and/or providing an exended or delayed release of ketamine as compared to ketamine exposure and/or administration, the method comprising administering to a subject in need thereof any one of the ketamine compounds or pharmaceutically acceptable salts of the compounds.

In some aspects, the composition provides reduced maximal exposure (Cmax) and/or reduced total exposure (AUC) to ketamine when administered intranasally at an equimolar dose to unconjugated ketamine. In another aspect, the composition provides reduced maximal exposure (Cmax) and/or reduced total exposure (AUC) to ketamine when administered intravenously at an equimolar dose to unconjugated ketamine. In yet another aspect, the composition provides reduced abuse potential or is resistant to abuse when administered intranasally and/or intravenously at an equimolar dose to unconjugated ketamine. In an aspect, the composition provides reduced maximal exposure (Cmax) and/or reduced total exposure (AUC) to norketamine when administered orally at an equimolar dose to unconjugated ketamine. In another aspect, the composition provides reduced maximal exposure (Cmax) and/or reduced total exposure (AUC) to norketamine when administered orally at a dose that provides therapeutically equivalent exposure to ketamine when compared to unconjugated ketamine. In yet another aspect, the composition provides an extended release or delayed release (longer Tmax) of ketamine after oral administration when compared to a therapeutically equivalent oral dose of unconjugated ketamine.

Advantages of certain aspects of the ketamine compounds and compositions of the present technology include, but are not limited to, reduced drug abuse potential, improved bioavailability by, for example, resisting conversion to norketamine, modulated pharmacokinetics that can, for example, decrease sharp peaks in ketamine plasma concentrations compared to unconjugated ketamine, reduced side effects, resistant to chemical or physical manipulation resulting in complete release of ketamine, reduced intersubject and/or intrasubject variability in plasma concentrations compared to unconjugated ketamine, improved dosage forms through modifications of the physical and chemical properties of the compounds, and the enablement of new routes of administration.

In some aspects, the present technology provides an immediate release of ketamine compounds that allows delivery of ketamine into the blood system of a human or animal in a therapeutically and pharmacokinetically bioequivalent manner upon administration. In other aspects, the ketamine compounds can result in improved oral bioavailability by reducing first-pass metabolism in the liver. The presently described technology, in at least one aspect, provides a slow/sustained/controlled/delayed release of ketamine into the blood system of a human or animal within a safe therapeutic window upon, for example, oral administration.

BRIEF DESCRIPTION OF THE DRAWINGS

Various aspects of the present disclosure will now be described, by way of example only, with reference to the attached Figures, wherein:

FIG. 1A depicts the oral plasma concentration of ketamine and FIG. 1B depicts the oral plasma concentration of norketamine, the major metabolite of ketamine.

FIG. 2A depicts the oral plasma concentration of ketamine and FIG. 2B depicts the oral plasma concentration of norketamine.

FIG. 3A depicts the oral plasma concentration of ketamine and FIG. 3B depicts the oral plasma concentration of norketamine.

FIG. 4A depicts the oral plasma concentration of ketamine and FIG. 4B depicts the oral plasma concentration of norketamine.

FIG. 5A depicts the oral plasma concentration of ketamine and FIG. 5B depicts the oral plasma concentration of norketamine.

FIG. 6A depicts the oral plasma concentration of ketamine and FIG. 6B depicts the oral plasma concentration of norketamine.

FIG. 7A depicts the oral plasma concentration of ketamine and FIG. 7B depicts the oral plasma concentration of norketamine.

FIG. 8A depicts the oral plasma concentration of ketamine and FIG. 8B depicts the oral plasma concentration of norketamine.

FIG. 9A depicts the oral plasma concentration of ketamine and FIG. 9B depicts the oral plasma concentration of norketamine.

FIG. 10A depicts the oral plasma concentration of ketamine and FIG. 10B depicts the oral plasma concentration of norketamine.

FIG. 11A depicts the oral plasma concentration of ketamine and FIG. 11B depicts the oral plasma concentration of norketamine.

FIG. 12A depicts the oral plasma concentration of ketamine and FIG. 12B depicts the oral plasma concentration of norketamine.

FIG. 13A depicts the intranasal plasma concentration of ketamine and FIG. 13B depicts the intranasal plasma concentration of norketamine.

FIG. 14A depicts the intranasal plasma concentration of ketamine and FIG. 14B depicts the intranasal plasma concentration of norketamine.

FIG. 15A depicts the intranasal plasma concentration of ketamine and FIG. 15B depicts the intranasal plasma concentration of norketamine.

FIG. 16A depicts the intranasal plasma concentration of ketamine and FIG. 16B depicts the intranasal plasma concentration of norketamine.

FIG. 17A depicts the intranasal plasma concentration of ketamine and FIG. 17B depicts the intranasal plasma concentration of norketamine.

FIG. 18A depicts the intranasal plasma concentration of ketamine and FIG. 18B depicts the intranasal plasma concentration of norketamine.

FIG. 19A depicts the intranasal plasma concentration of ketamine and FIG. 19B depicts the intranasal plasma concentration of norketamine.

FIG. 20A depicts the intranasal plasma concentration of ketamine and FIG. 20B depicts the intranasal plasma concentration of norketamine.

FIG. 21A depicts the intravenous plasma concentration of ketamine and FIG. 21B depicts the intravenous plasma concentration of norketamine.

FIG. 22A depicts the intravenous plasma concentration of ketamine and FIG. 22B depicts the intravenous plasma concentration of norketamine.

DETAILED DESCRIPTION

Figure 1A:
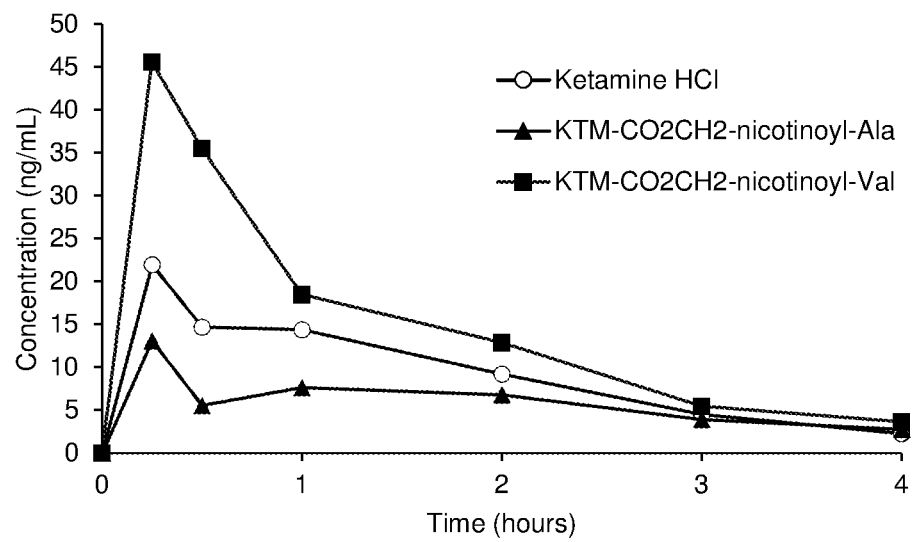
FIGS. 1A and 1B depict oral plasma concentration-time profiles of unconjugated ketamine as compared to KTM-CO$_2$CH$_2$-nicotinoyl-Ala and KTM-CO$_2$CH$_2$-nicotinoyl-Val.

The present technology describes, in general, novel compounds and compositions of ketamine, salts thereof, other derivatives thereof, and combinations thereof. These novel compounds comprise nicotinic acid, isonicotinic acid, pyridine, morpholine, phosphate, oxoacid, amino acid, and/or peptide compounds that are chemically conjugated to ketamine. The present technology also generally relates to methods of making these new compounds and compositions comprising the ketamine compounds.

It is to be understood that this disclosure is not limited to the particular methodology, protocols, and reagents described herein and as such may vary. It is also to be understood that the terminology used herein is for the purpose of describing particular embodiments only and is not intended to limit the scope of the present disclosure or the appended claims.

As used herein and in the appended claims, the singular forms "a," "an," and "the" include plural reference unless the context clearly indicates otherwise.

The term "about" is used in connection with a numerical value throughout the specification and the claims denote an interval of accuracy, familiar and acceptable to a person skilled in the art. In general, such an interval of accuracy is +/−10%.

Unless defined otherwise, all technical and scientific terms used herein have the same meaning as commonly understood to one of ordinary skill in the art to which this disclosure belongs.

The use of the term "ketamine" herein means 2-(2-chlorophenyl)-2-(methylamino)cyclohexanone, including salt forms thereof. In some aspects, the compounds contain ketamine in a racemic mixture. In other aspects, the ketamine compounds are not in a racemic mixture. Depending on the chemical structure of the linkers and nicotinic acid, isonicotinic acid, pyridine, morpholine, phosphate, oxoacid, amino acid, and/or peptide compounds, as well as the chiral composition of the ketamine to which they are attached, the resulting compounds can be optically active mixtures of isomers, racemic mixtures, single isomers or combinations thereof.

The term "oxoacid" (i.e., oxyacids, oxo acids, oxy acids, oxiacids, oxacids) refers to a class of compounds that contain oxygen, at least one other element, and at least one hydrogen bound to oxygen, and which produce a conjugate base by loss of positive hydrogen ion(s) (protons).

"Amino acids" refers to organic compounds containing both a carboxyl (—COOH) and amino (—NH$_2$) group, and a variable side chain group. Amino acids that may be used in the present technology can be natural, standard, non-standard, unusual, synthetic, and/or essential amino acids, and can be an L-amino acid or a D-amino acid, or a combination thereof. Examples of amino acids for use in the practice of the present technology include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, homoarginine, citrulline, homocitrulline, homoserine, theanine, γ-aminobutyric acid, 6-aminohexanoic acid, sarcosine, carnitine, 2-aminoadipic acid, pantothenic acid, taurine, hypotaurine, lanthionine, thiocysteine, cystathionine, homocysteine, β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), 2-aminoisobutyric acid, isovaline, di-N-ethylglycine, N-methyl-alanine, L-abrine, 4-hydroxyproline, 5-hydroxylysine, 3-hydroxyleucine, 4-hydroxyisoleucine, 5-hydroxy-L-tryptophan, 1-aminocyclopropyl-1-carboxylic acid, azetidine-2-carboxylic acid, pipecolic acid, allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino-propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, 4-(dimethylamino)cinnamic acid, 2-pyridylalanine (2-Pal), and 3-pyridylalanine (3-Pal).

As used herein, the term "prodrug" refers to a substance converted from an inactive form of a drug to an active drug in the body by a chemical or biological reaction. In an aspect of the present technology, the prodrug is a conjugate of at least one drug, ketamine, and at least one ligand, nicotinic acid, for example. Thus, in an aspect of the present technology, the ketamine compounds are prodrugs.

Prodrugs are often useful because, in some aspects, they may be easier to administer or process than the parent drug. For example, they may be more bioavailable by oral administration, whereas the parent drug is not. The prodrug may also have improved solubility and/or stability in pharmaceutical compositions over the parent drug. An embodiment of a prodrug would be a ketamine compound that is metabolized to release the active moiety. In certain aspects, upon in vivo administration, a prodrug is chemically converted to the biologically, pharmaceutically, or therapeutically more active form of the compound. In certain aspects, a prodrug is enzymatically or chemically metabolized by one or more steps or processes to the biologically, pharmaceutically, or therapeutically more active form of the compound. To produce a prodrug, a pharmaceutically active compound is modified such that the active compound will be regenerated upon in vivo administration. The prodrug is designed to alter the metabolism, pharmacokinetics, or the transport characteristics of a drug in certain aspects. to reduce side-effects or toxicity, to improve bioavailability and/or water solubility, to improve the flavor of a drug, or to alter other characteristics or properties of a drug in other discrete aspects.

General Structures

In accordance with some aspects, the present technology provides ketamine in a compound form. More specifically, the ketamine compound comprises at least one organic compound covalently bonded or attached to ketamine. The general structure of the ketamine compounds of the present technology can be represented by the following general Formula I:

Formula I

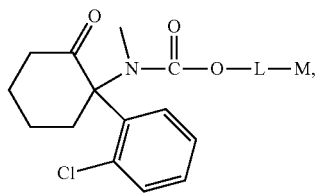

where L is selected from alkyl, alkenyl, alkynyl, alkoxy, alkylamino, aryl, substituted aryl, and cycloalkyl;

where M is selected from

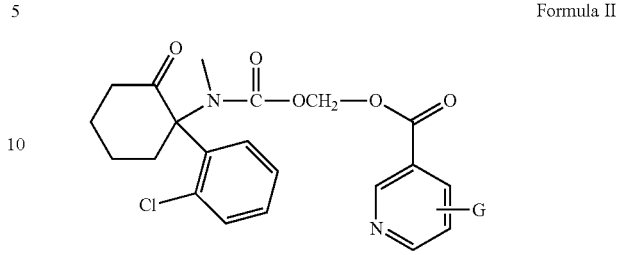

where G is selected from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, and thiol;

where Z is selected from hydrogen,

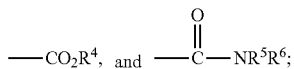

and where $R^1$, $R^2$, $R^3$, $R^4$, $R^5$, and $R^6$ are independently selected from hydrogen, alkyl, alkenyl, alkynyl, alkoxy, alkylamino, aryl, substituted aryl, and cycloalkyl.

In some aspects, the compound has the following structural Formula II:

Formula II

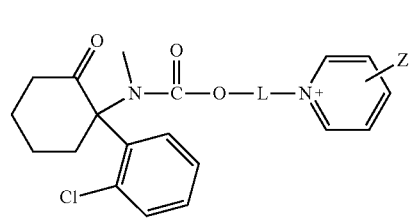

where G is selected from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, and thiol.

In some aspects, the compound has the following structural Formula III:

Formula III

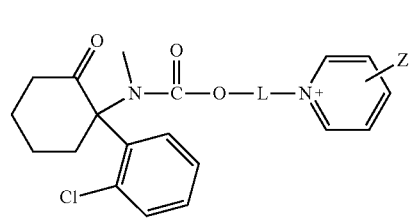

where Z is selected from hydrogen,

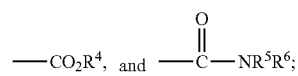

and where $R^4$, $R^5$, and $R^6$ are independently selected from hydrogen, alkyl, alkenyl, alkynyl, alkoxy, alkylamino, aryl, substituted aryl, and cycloalkyl.

In some aspects, the compound has the following structural Formula IV:

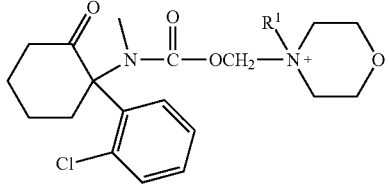

Formula IV where $R^1$ is selected from hydrogen, alkyl, alkenyl, alkynyl, alkoxy, alkylamino, aryl, substituted aryl, and cycloalkyl.

In some aspects, the compound has the following structural Formula V:

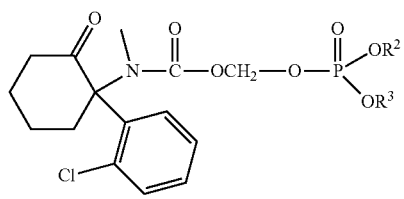

Formula V where $R^2$ and $R^3$ are independently selected from hydrogen, alkyl, alkenyl, alkynyl, alkoxy, alkylamino, aryl, substituted aryl, and cycloalkyl.

In some aspects, the compound is nicotinate-$CH_2$OCO-KTM having the following structural Formula VIa, or isonicotinate-$CH_2$OCO-KTM having the following structural Formula VIb:

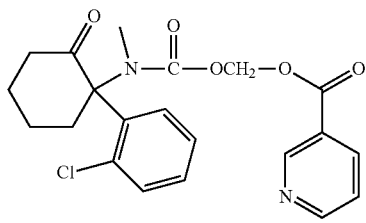

Formula VIa

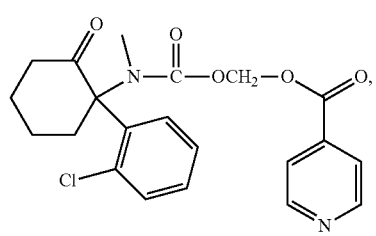

Formula VIb or a pharmaceutically acceptable salt thereof.

In some aspects, the compound is KTM-$CO_2CH_2$—N-Me-Morpholine having the following structural Formula VIII:

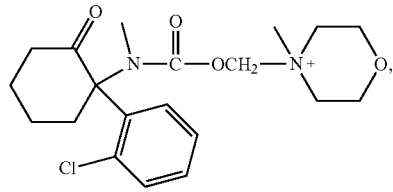

Formula VIII or a pharmaceutically acceptable salt thereof.

In some aspects, the compound is Phosphate-$CH_2$OCO-KTM having the following structural Formula IX:

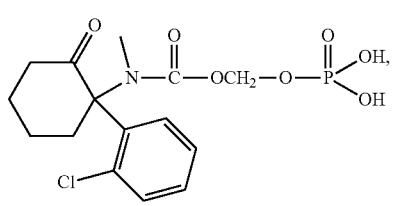

Formula IX or a pharmaceutically acceptable salt thereof.

In some aspects, the compound has the following structural Formula VIIa:

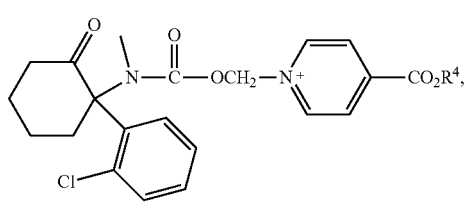

Formula VIIa where $R^4$ has the same meaning above, or a pharmaceutically acceptable salt thereof. Examples of compounds having the structure of Formula VIIa include, but are not limited to, ketamine-$CO_2CH_2$-isonicotinic acid and ketamine-$CO_2CH_2$-isonicotinate(tBu).

In some aspects, the compound has the following structural Formula VIIb:

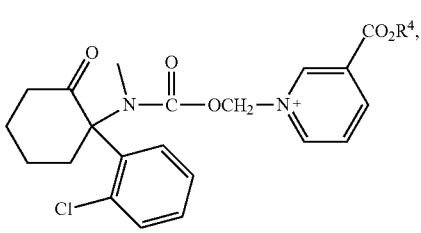

Formula VIIb where $R^4$ has the same meaning above, or a pharmaceutically acceptable salt thereof. Examples of compounds having the structure of Formula VIIb include, but are not limited to, ketamine-$CO_2CH_2$-niacin (nicotinic acid), ketamine-$CO_2CH_2$-nicotinate(tBu), ketamine-$CO_2$—$CH_2$-nicotinate(Et), and ketamine-$CO_2CH_2$-nicotinate(Me).

In some aspects, the compound has the following structural Formula VIIc:

Formula VIIc

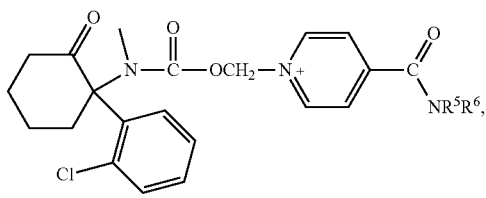

where $R^5$ and $R^6$ have the same meaning above, or a pharmaceutically acceptable salt thereof. Examples of compounds having the structure of Formula VIIc include, but are not limited to, ketamine-$CO_2CH_2$-isonicotinoyl-ornithine, ketamine-$CO_2CH_2$-isonicotinoyl-sarcosine, ketamine-$CO_2CH_2$-isonicotinoyl-N-Me-alanine, ketamine-$CO_2CH_2$-isonicotinoyl-Gly-Ala, and ketamine-$CO_2CH_2$-isonicotinoyl-Phe-Phe.

In some aspects, the compound has the following structural Formula VIId:

Formula VIId

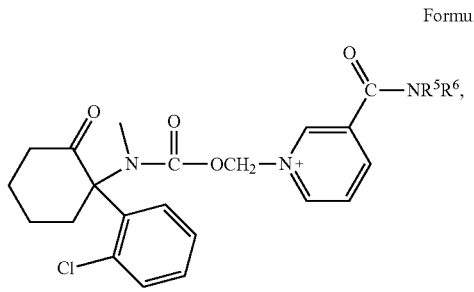

where $R^5$ and $R^6$ have the same meaning above, or a pharmaceutically acceptable salt thereof. Examples of compounds having the structure of Formula VIId include, but are not limited to, ketamine-$CO_2CH_2$-nicotinoyl-sarcosine, ketamine-$CO_2CH_2$-nicotinoyl-glycine, ketamine-$CO_2CH_2$-nicotinoyl-alanine, ketamine-$CO_2CH_2$-nicotinoyl-valine, ketamine-$CO_2CH_2$-nicotinoyl-isoleucine, ketamine-$CO_2CH_2$-nicotinoyl-proline, ketamine-$CO_2CH_2$-nicotinoyl-lysine, ketamine-$CO_2CH_2$-nicotinoyl-hydroxyproline, ketamine-$CO_2CH_2$-nicotinoyl-tyrosine, ketamine-$CO_2CH_2$-nicotinoyl-phenylalanine, ketamine-$CO_2CH_2$-nicotinoyl-glutamine, ketamine-$CO_2CH_2$-nicotinoyl-asparagine, ketamine-$CO_2CH_2$-nicotinoyl-aspartic acid, ketamine-$CO_2CH_2$-nicotinoyl-glutamic acid, ketamine-$CO_2CH_2$-nicotinoyl-ornithine, ketamine-$CO_2CH_2$-nicotinoyl-serine, ketamine-$CO_2CH_2$-nicotinoyl-threonine, ketamine-$CO_2CH_2$-nicotinoyl-leucine, ketamine-$CO_2CH_2$-nicotinoyl-methionine, ketamine-$CO_2CH_2$-nicotinoyl-arginine, ketamine-$CO_2CH_2$-nicotinoyl-morpholine, ketamine-$CO_2CH_2$—N-Me-diethanolamine, and ketamine-$CO_2CH_2$-nicotinoyl-3-aminobenzoic acid.

In some aspects, the pharmaceutically acceptable salt of the ketamine compound is a single salt or a mixed salt, where the one or more of the salts are selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, buyrate, canmphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esykate, glycolate, thiocyanate, undecylenate, sodium, potassium, calcium, magnesium, zinc, aluminum, lithium, cholinate, lysinium, ammonium, troethamine, and a mixture thereof.

The ketamine compounds of the present technology can be formulated into compositions for administration to a human or animal. The compositions may further comprise one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

Physiological Benefits

The above-defined ketamine compounds can be given orally and, upon administration, release the active ketamine after being hydrolyzed in the body. Since many of the nicotinic acid, isonicotinic acid, pyridine, morpholine, phosphate, oxoacid, amino acid, and/or peptide compounds ("ligands") of this invention are naturally occurring metabolites or mimetics thereof, or pharmaceutically active compounds, these ketamine compounds can be easily recognized by physiological systems resulting in hydrolysis and release of ketamine. The claimed compounds themselves have no or limited pharmacological activity and consequently may follow a metabolic pathway that differs from the pharmaceutically active ketamine drug. By choosing suitable ligands, the release of ketamine into the systemic circulation can be controlled even when the ketamine compound is administered via routes other than oral. In one embodiment, the ketamine compound would release ketamine similar to free or unmodified ketamine. In another embodiment, the modified ketamine would be released in a controlled or sustained manner. This controlled release can potentially alleviate certain side-effects and improve upon the safety profile of the parent drug. These side-effects may include, dizziness, lightheadedness, drowsiness, nausea, vomiting, constipation, stomach pain, elevation of blood pressure and pulse rate, depression of respiration, diplopia and nystagmus, severe irritative and inflammatory urinary tract and bladder symptoms, enhanced skeletal muscle tone, anorexia, or anaphylaxis. In addition, ketamine is also prone to substance abuse.

Recreational abuse of ketamine is common in abusers seeking euphoria ("rush", "high"). Over time, the drug abuser often increases the ketamine dosages to attain more powerful "highs" or to compensate for tolerance to the drug following repeat exposures. Rapid and large increase in ketamine plasma concentrations after administration contributes to its likelihood of being abused. Because ketamine abusers seek a fast high, they typically snort or inject ketamine, since these routes of administration offer the most rapid, intense high due to its superior bioavailability compared to oral consumption. In some aspects, ketamine that is conjugated with a suitable ligand exhibits no rapid spikes in blood levels after oral administration that is sought by a potential drug abuser. When taken orally, certain prodrugs may have a delayed $T_{max}$ and possibly lower $C_{max}$ than the parent drug and therefore lack or reduce the feeling of a "rush" when taken orally, even at high doses. In another embodiment, ketamine conjugated with appropriate ligands of this invention is not hydrolyzed efficiently when administered via non-oral routes. As a result, they do not generate high plasma or blood concentrations of released ketamine when injected or snorted compared to unconjugated ketamine administered via these routes. Furthermore, since the ligands of this invention are bound covalently to ketamine, the ketamine molecule is not liberated by any type of physical manipulation as is possible, for example, by grinding up or crushing some other types of drug formulations (e.g., beads) that are intended to deter non-oral routes of abuse or to provide extended-release properties.

Another common safety issue with unmodified ketamine that may be eliminated or reduced with ketamine conjugates is emergence reactions. Emergence reactions to ketamine include psychological manifestations that vary in severity between pleasant dream-like states, vivid imagery, hallucinations, and emergence delirium. These states have been accompanied by confusion, excitement, and irrational behavior. In some aspects, ketamine compounds may reduce the occurrence of emergence reactions by modifying the pharmacokinetics such that ketamine is released from the prodrug in a controlled manner without the typical spike in blood concentrations and consequent rapid elimination that is thought to contribute to emergence reactions.

Ketamine abuse has also been associated with severe, irreversible bladder and urinary tract symptoms such as cystitis. In some aspects, ketamine prodrugs can eliminate or reduce this side effect by changing the rate at which ketamine is absorbed and/or eliminated. In other aspects, the ligand that is conjugated to ketamine has anti-inflammatory actions that may counteract bladder and urinary tract symptoms.

In some aspects, ketamine prodrugs may be useful to extend the duration of action of released ketamine. This can be achieved via any route of administration. When ketamine is conjugated to certain ligands, the majority or at least some of the resulting prodrug is stable through the first pass through the liver following oral administration but slowly metabolizes in the systemic circulation to release ketamine. This can result in improved oral bioavailability since there is less or no conversion to, for example, norketamine in the liver compared to unconjugated ketamine, which is extensively metabolized to norketamine following oral administration. In some aspects, ketamine compounds can be administered intravenously. This may result in complete bioavailability of the inactive prodrug, which is slowly metabolized to release pharmacologically active ketamine. This may be preferable for medical uses outside of anesthesia since there is no rapid sedation that is produced when certain conjugated ketamines are injected. In other aspects, the ketamine compound can be administered intranasally. While intranasal administration of unconjugated ketamine can result in profound sedation due to the rapid absorption of active ketamine through the nasal mucosa and bypassing the first pass through the liver, ketamine compounds have little to no pharmacological activity and are slowly metabolized to release ketamine in vivo. This can be therapeutically preferable for uses other than anesthesia since it will limit the profound sedation that could otherwise be dangerous as a take-home medication that is intended to be administered by the patient. In other aspects, ketamine compounds can be administered via intramuscular injection. While intramuscular injection of unconjugated ketamine can result in profound sedation due to the rapid absorption of active ketamine through vascularized muscle tissue and bypassing the first pass through the liver, ketamine compounds have little to no pharmacological activity and are slowly metabolized to release ketamine in vivo. This can be therapeutically preferable for uses other than anesthesia since it will limit profound sedation produced by the parent drug and provide low and steady unconjugated ketamine over a longer period of time.

Figure 1B:
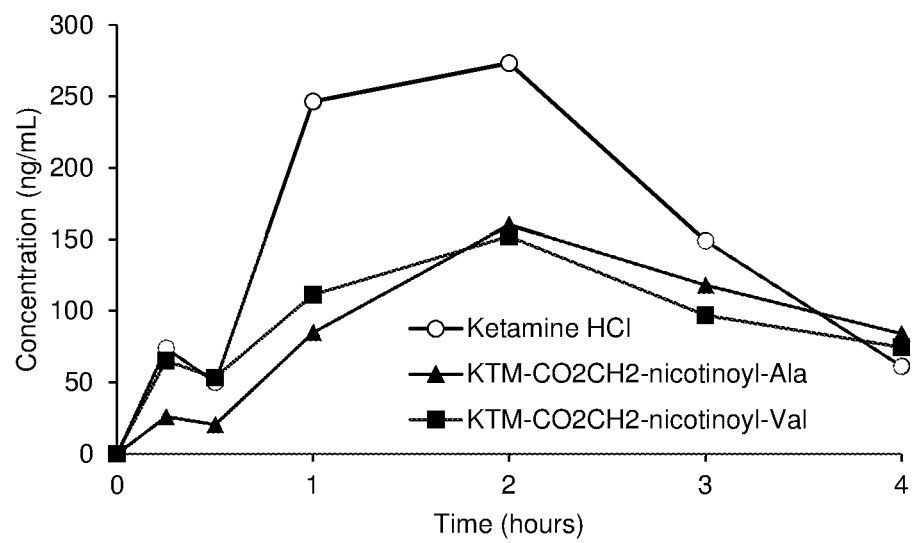
Figure 2A:
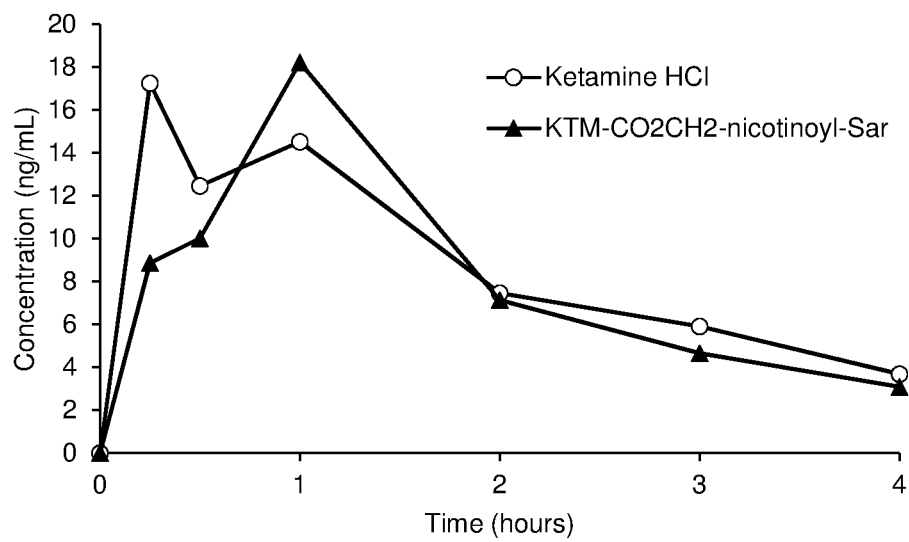
FIGS. 2A and 2B depict oral plasma concentration-time profiles of unconjugated ketamine as compared to KTM-CO$_2$CH$_2$-nicotinoyl-Sar.
Figure 2B:
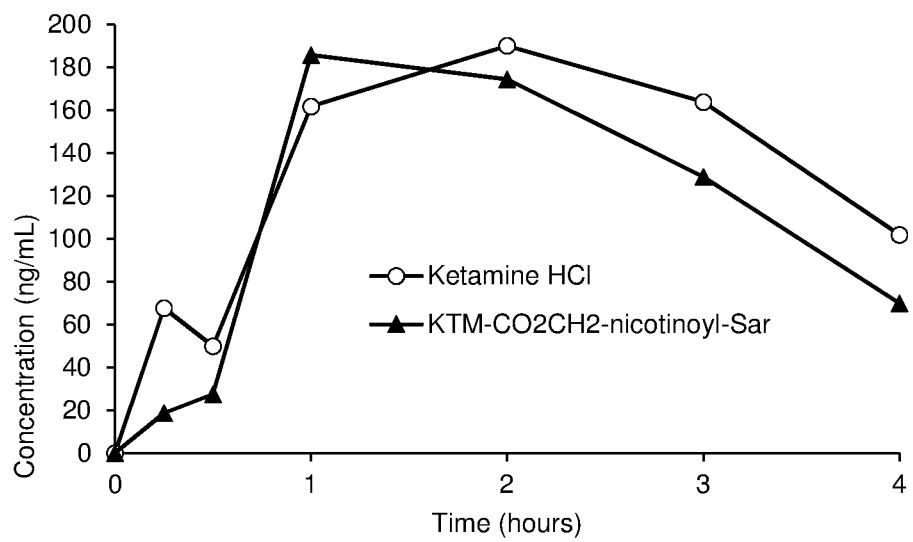
Figure 3A:
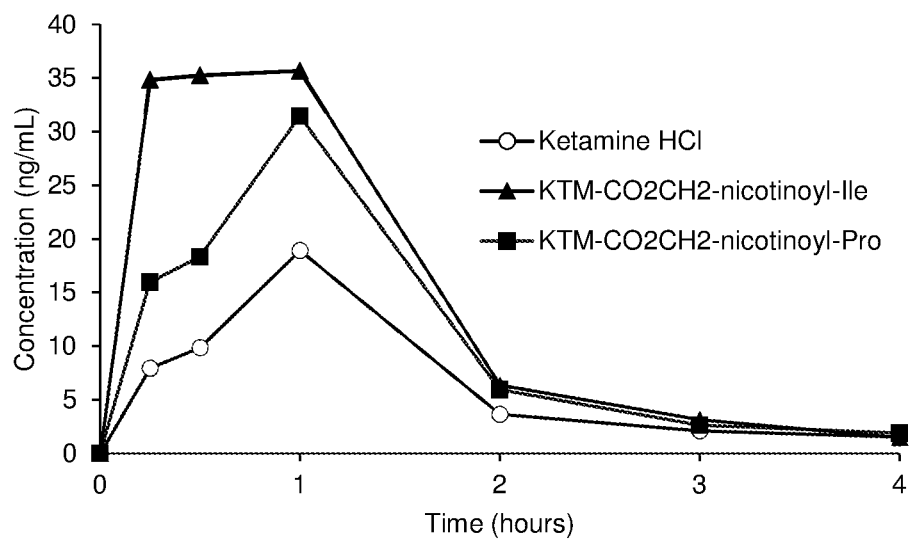
FIGS. 3A and 3B depict oral plasma concentration-time profiles of unconjugated ketamine as compared to KTM-CO$_2$CH$_2$-nicotinoyl-Ile and KTM-CO$_2$CH$_2$-nicotinoyl-Pro.
Figure 3B:
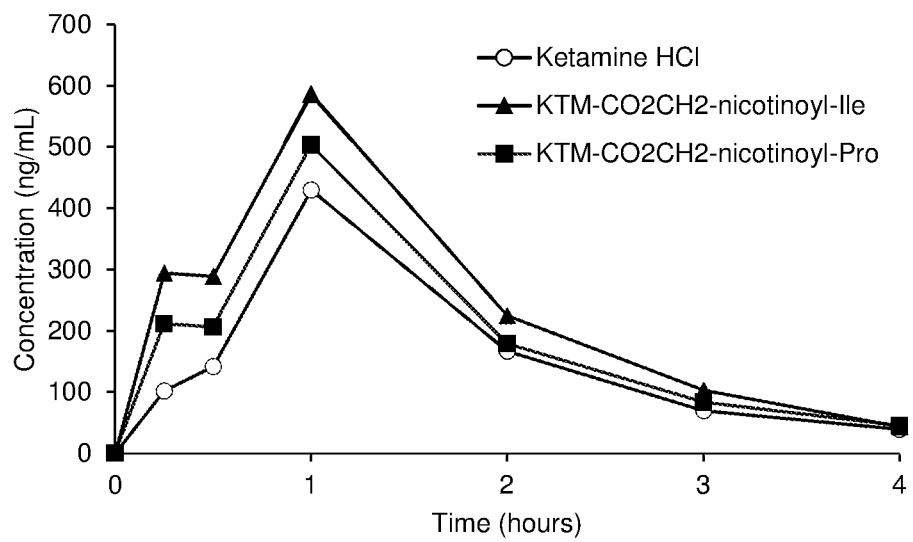
Figure 4A:
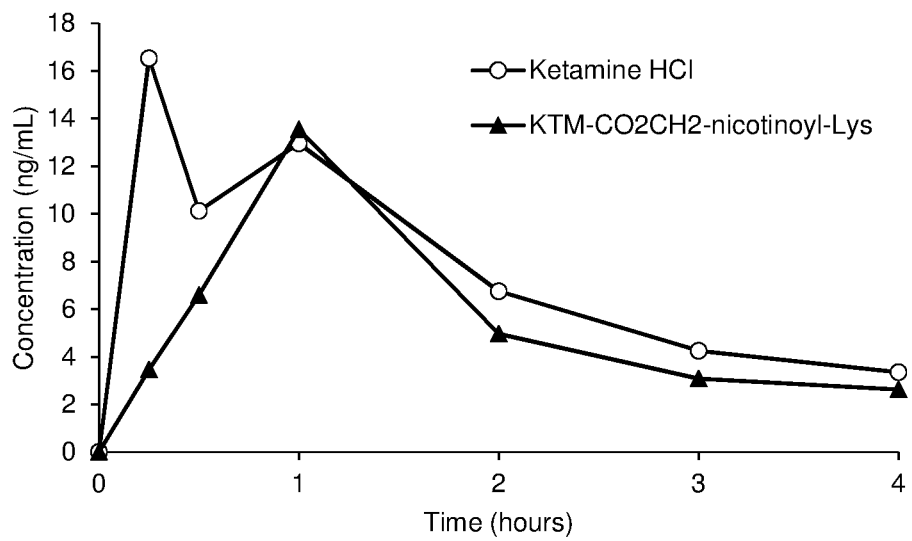
FIGS. 4A and 4B depict oral plasma concentration-time profiles of unconjugated ketamine as compared to KTM-CO$_2$CH$_2$-nicotinoyl-Lys.
Figure 4B:
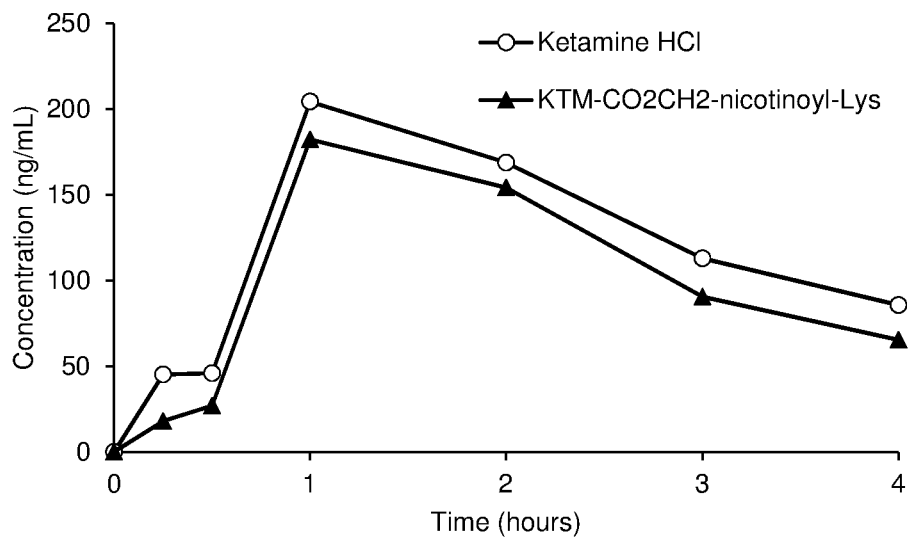
Figure 5A:
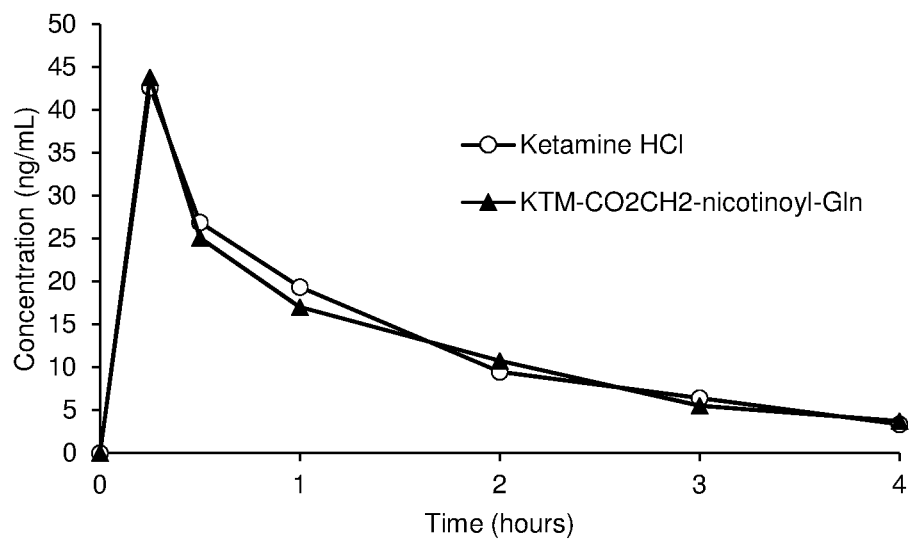
FIGS. 5A and 5B depict oral plasma concentration-time profiles of unconjugated ketamine as compared to KTM-CO$_2$CH$_2$-nicotinoyl-Gln.
Figure 5B:
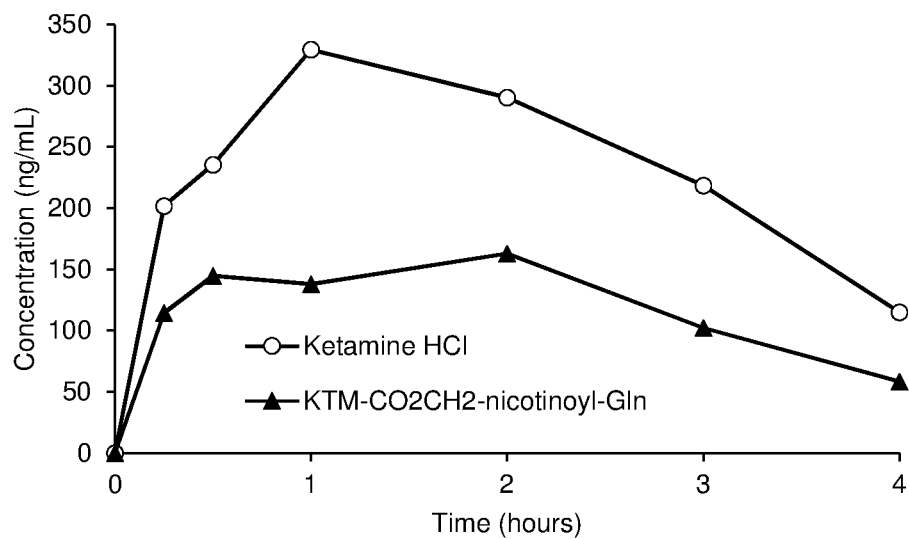
Figure 6A:
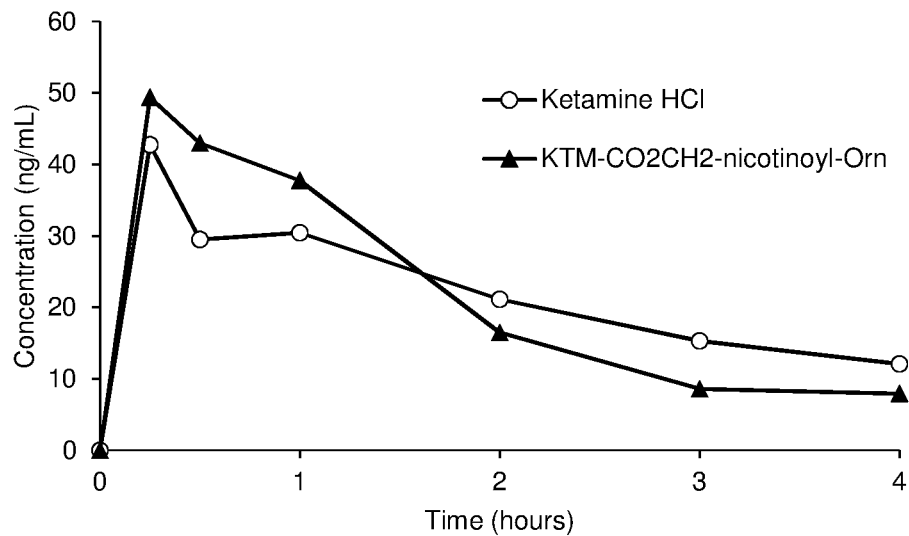
FIGS. 6A and 6B depict oral plasma concentration-time profiles of unconjugated ketamine as compared to KTM-CO$_2$CH$_2$-nicotinoyl-Orn.
Figure 6B:
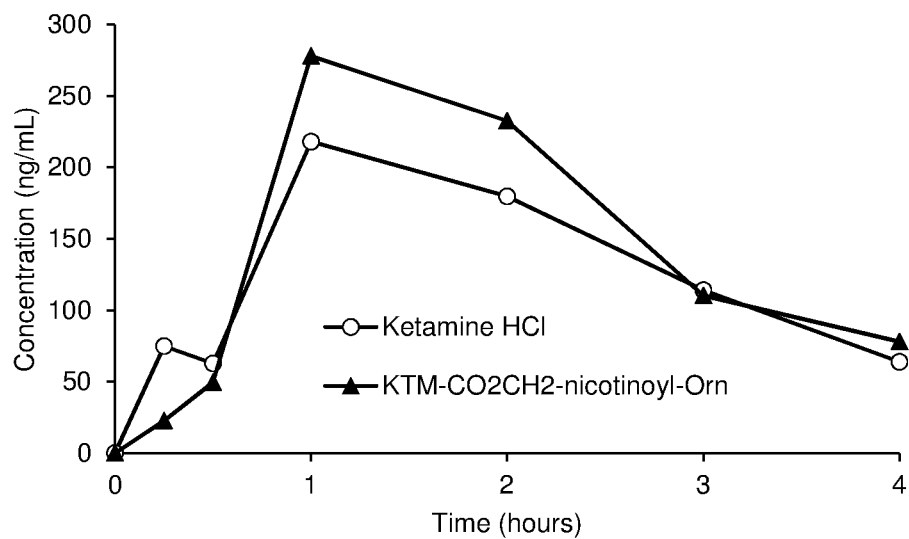
Figure 7A:
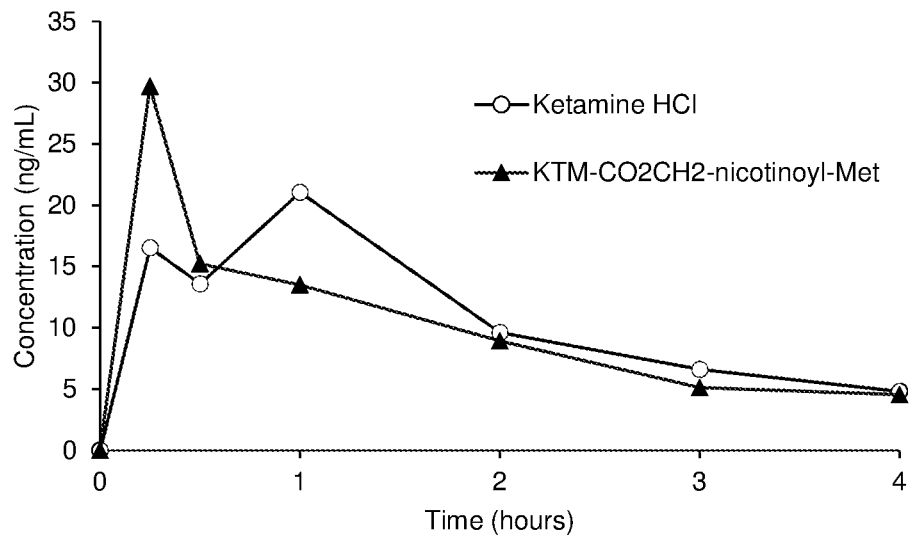
FIGS. 7A and 7B depict oral plasma concentration-time profiles of unconjugated ketamine as compared to KTM-CO$_2$CH$_2$-nicotinoyl-Met.
Figure 7B:
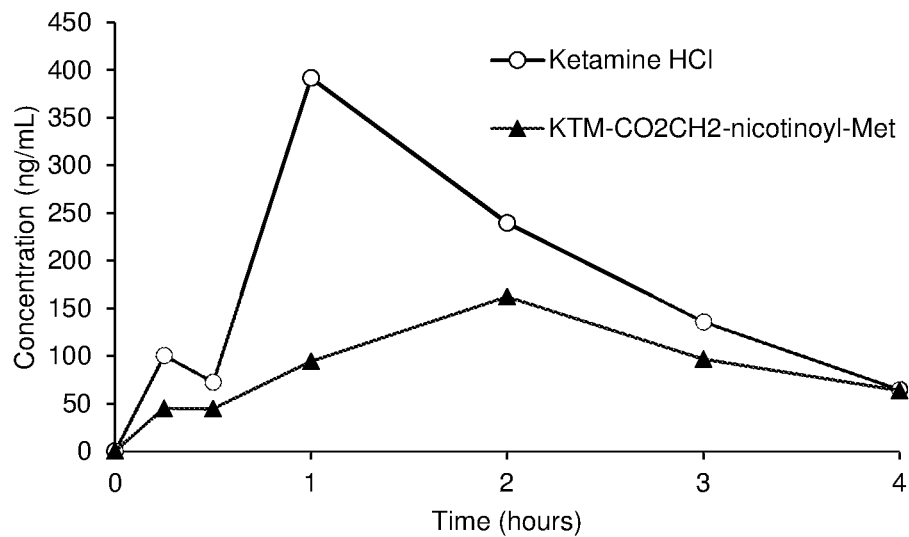
Figure 8A:
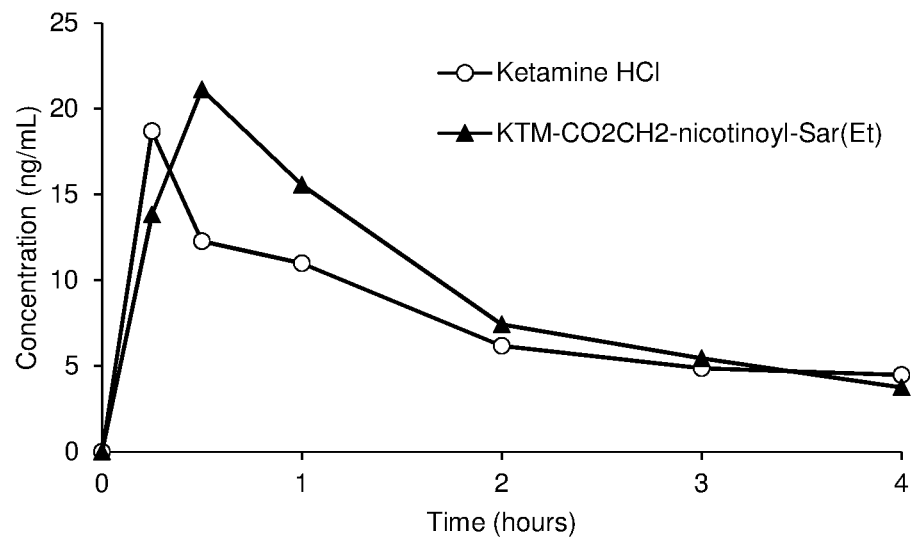
FIGS. 8A and 8B depict oral plasma concentration-time profiles of unconjugated ketamine as compared to KTM-CO$_2$CH$_2$-nicotinoyl-Sar(Et).
Figure 8B:
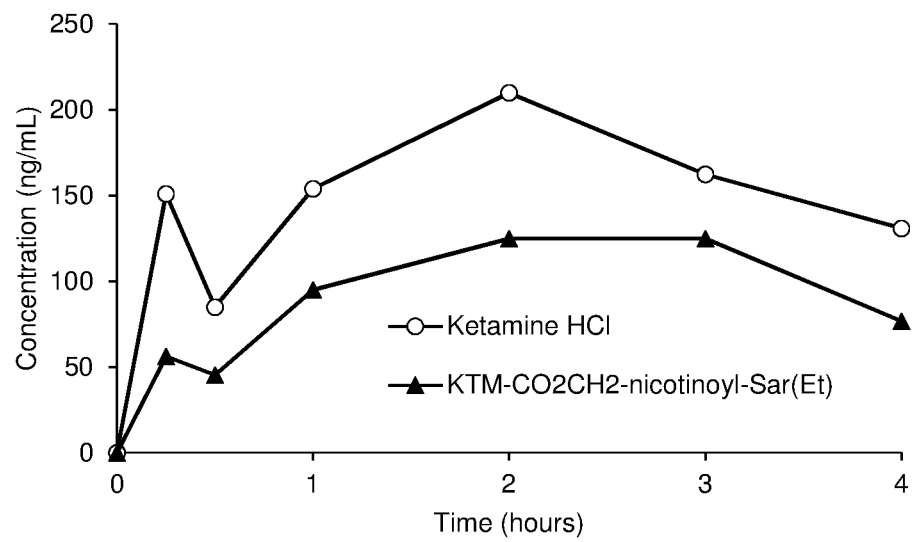
Figure 9A:
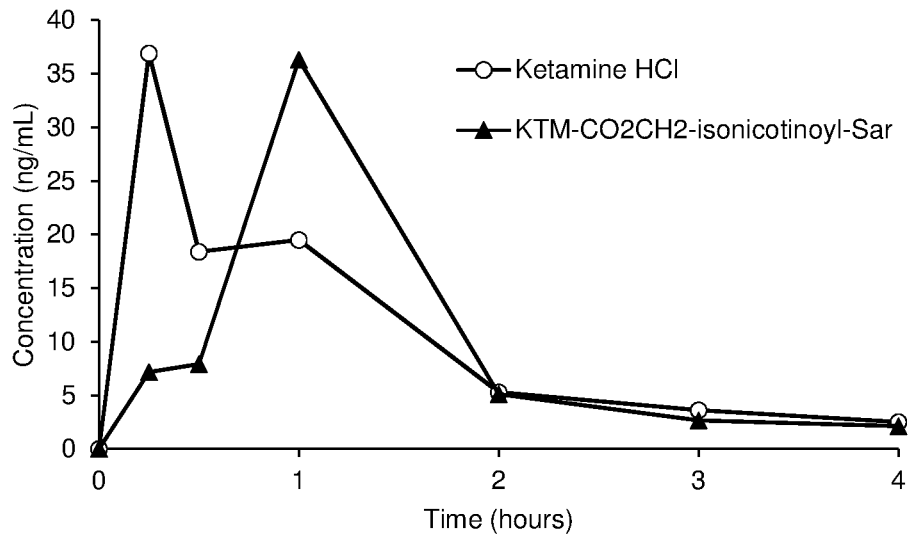
FIGS. 9A and 9B depict oral plasma concentration-time profiles of unconjugated ketamine as compared to KTM-CO$_2$CH$_2$-isonicotinoyl-Sar.
Figure 9B:
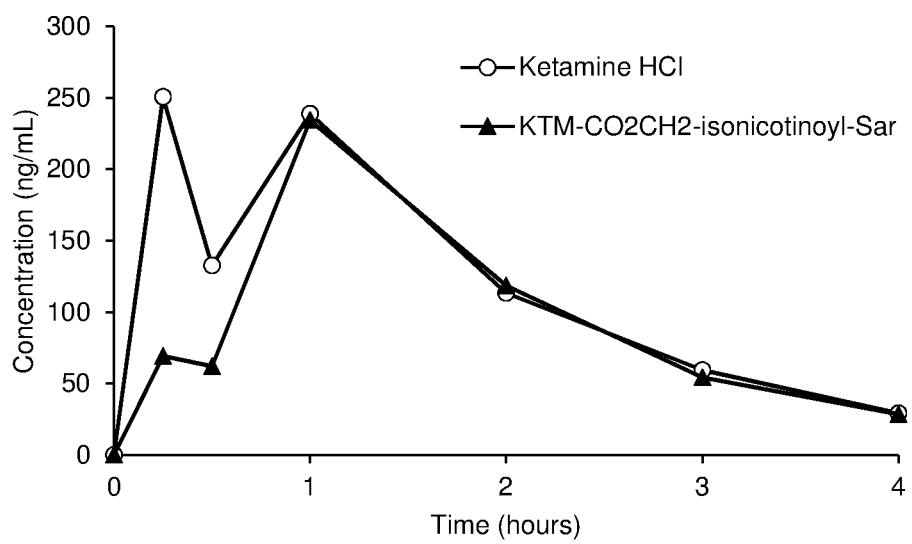
Figure 10A:
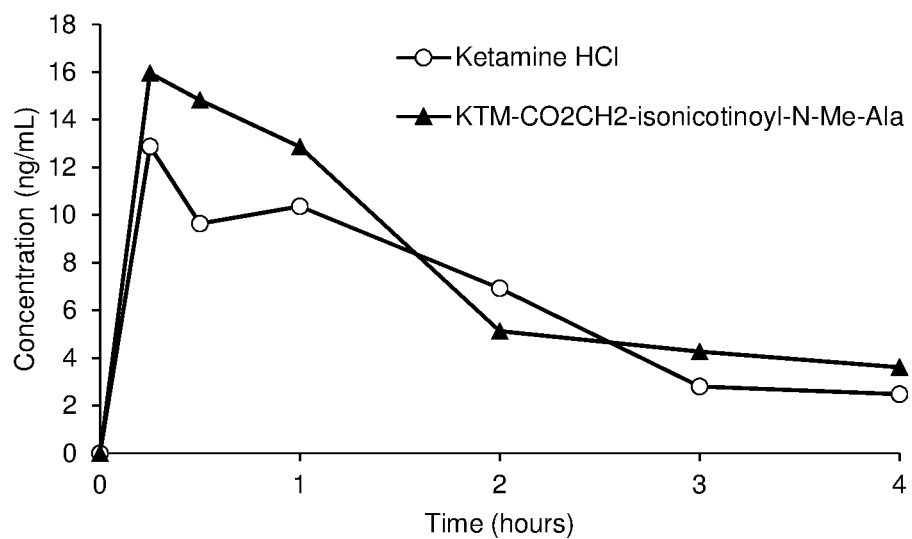
FIGS. 10A and 10B depict oral plasma concentration-time profiles of unconjugated ketamine as compared to KTM-CO$_2$CH$_2$-isonicotinoyl-N-Me-Ala.
Figure 10B:
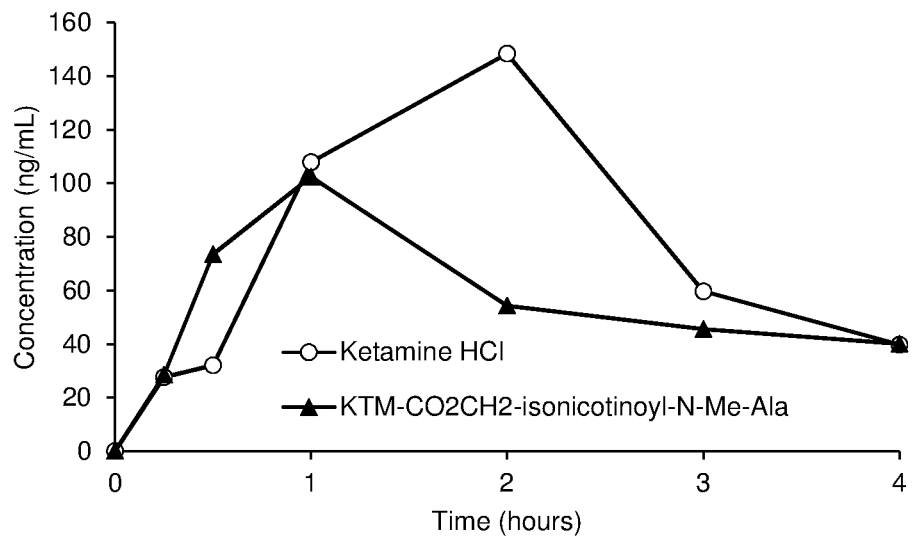
Figure 11A:
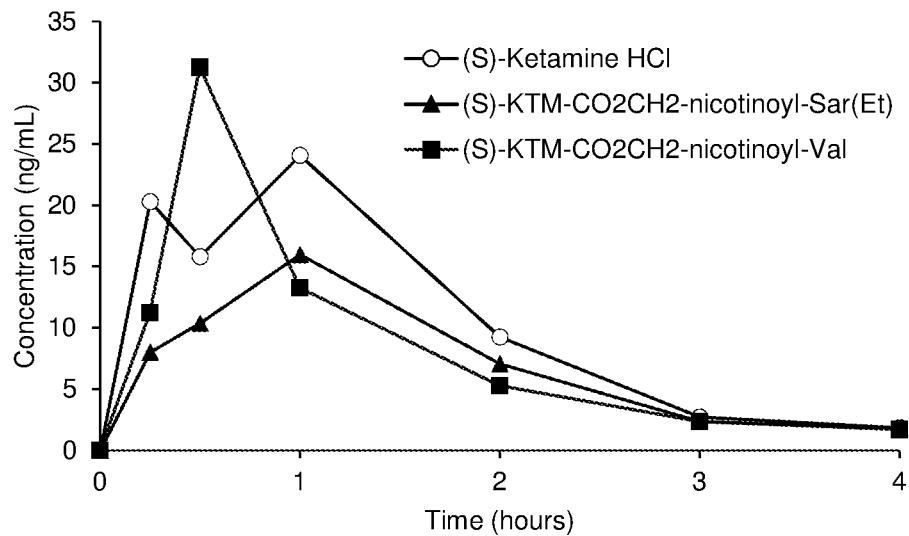
FIGS. 11A and 11B depict oral plasma concentration-time profiles of unconjugated (S)-ketamine as compared to (S)-KTM-CO$_2$CH$_2$-nicotinoyl-Sar(Et) and (S)-KTM-CO$_2$CH$_2$-nicotinoyl-Val.
Figure 11B:
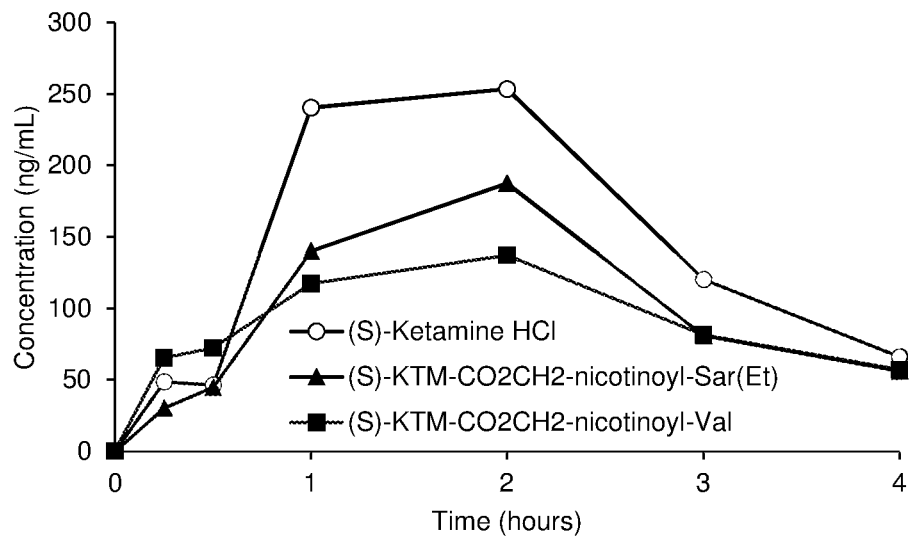
Figure 12A:
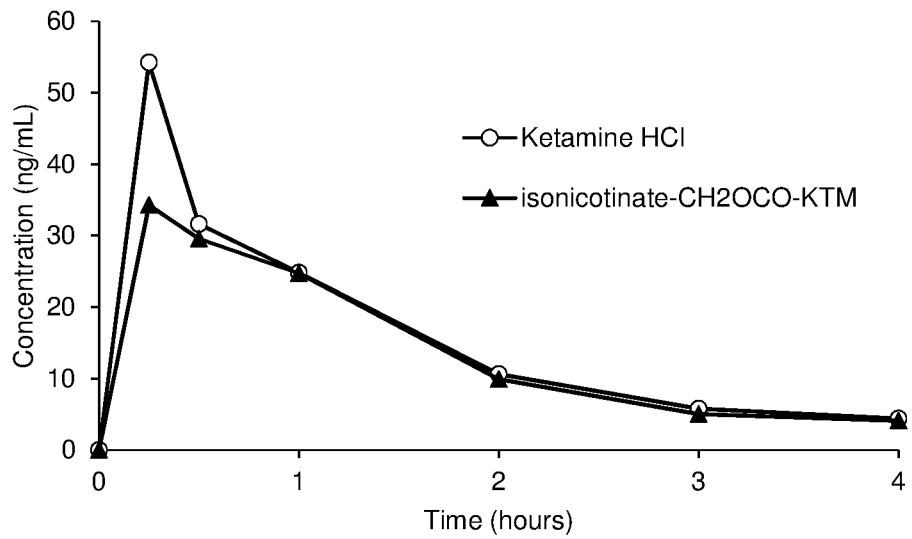
FIGS. 12A and 12B depict oral plasma concentration-time profiles of unconjugated ketamine as compared to isonicotinate-CH$_2$OCO-KTM.
Figure 12B:
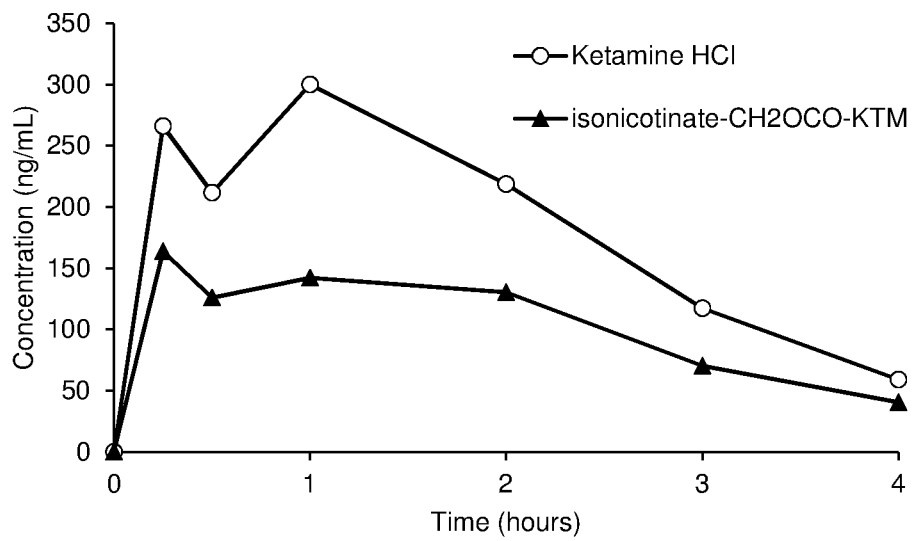
Figure 13A:
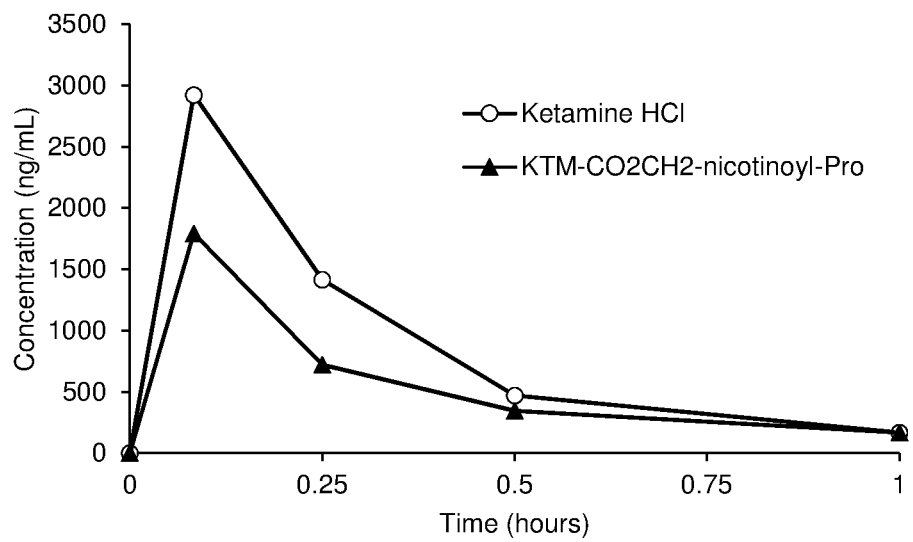
FIGS. 13A and 13B depict intranasal plasma concentration-time profiles of unconjugated ketamine as compared to KTM-CO$_2$CH$_2$-nicotinoyl-Pro.
Figure 13B:
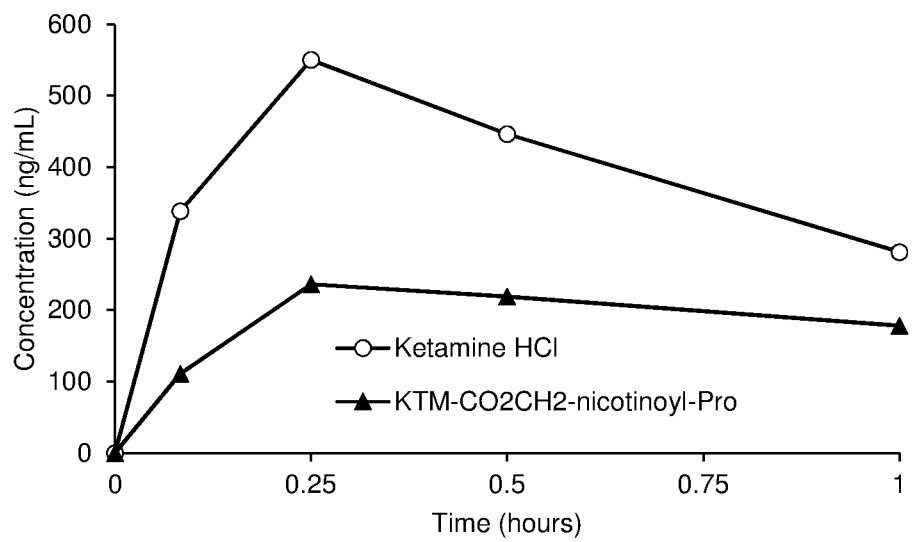
Figure 14A:
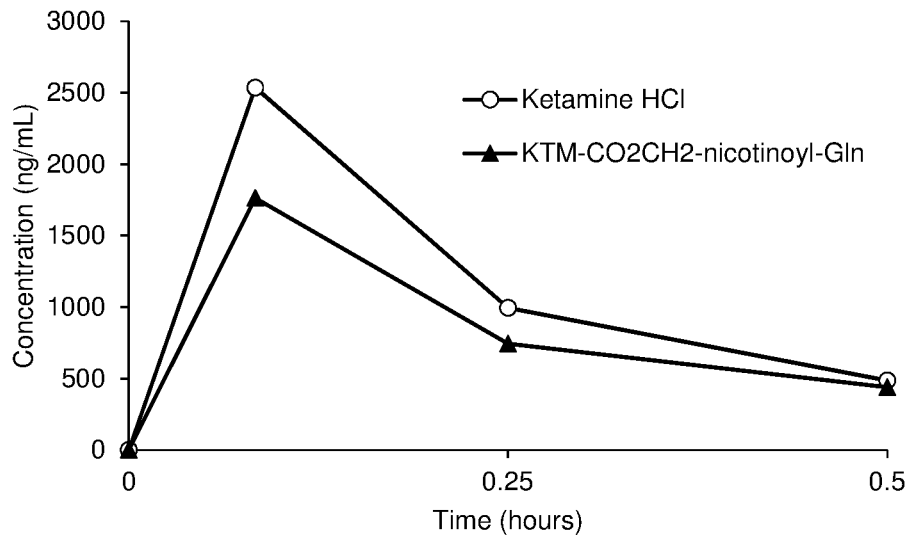
FIGS. 14A and 14B depict intranasal plasma concentration-time profiles of unconjugated ketamine as compared to KTM-CO$_2$CH$_2$-nicotinoyl-Gln.
Figure 14B:
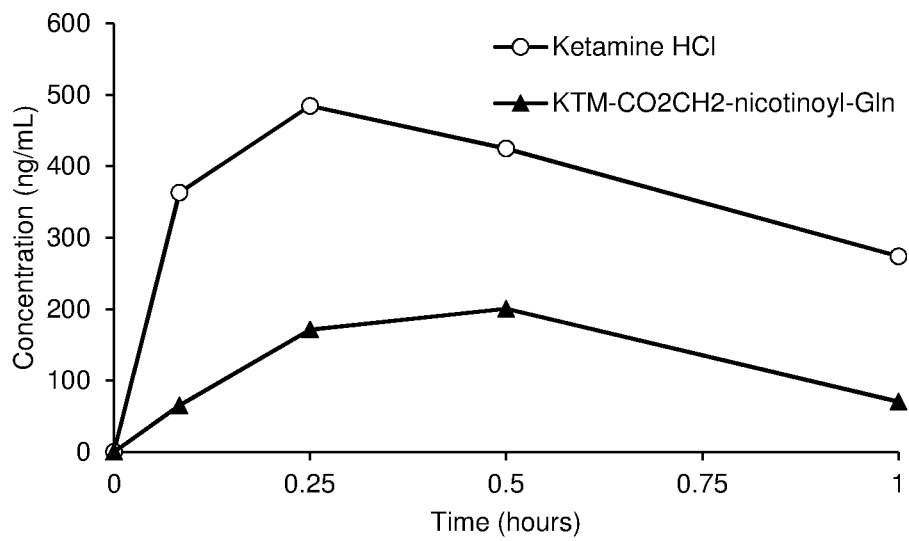
Figure 15A:
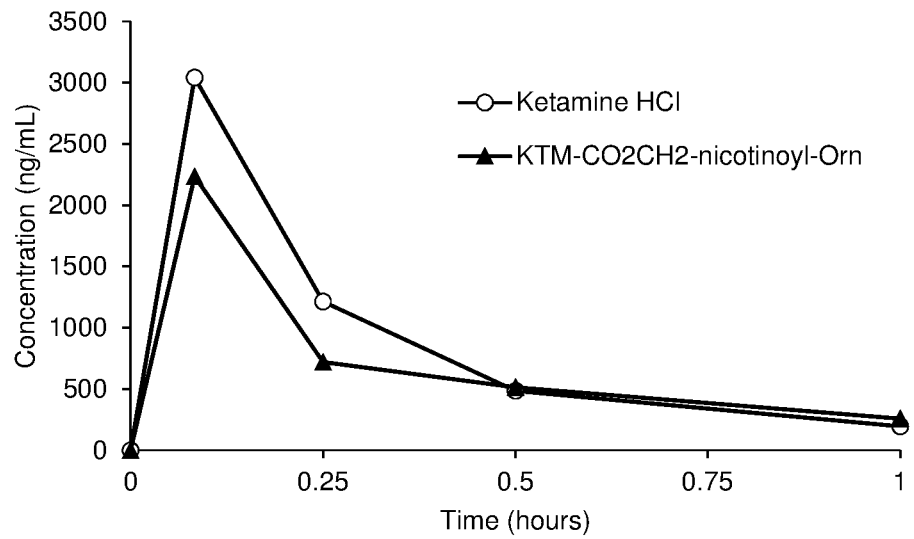
FIGS. 15A and 15B depict intranasal plasma concentration-time profiles of unconjugated ketamine as compared to KTM-CO$_2$CH$_2$-nicotinoyl-Orn.
Figure 15B:
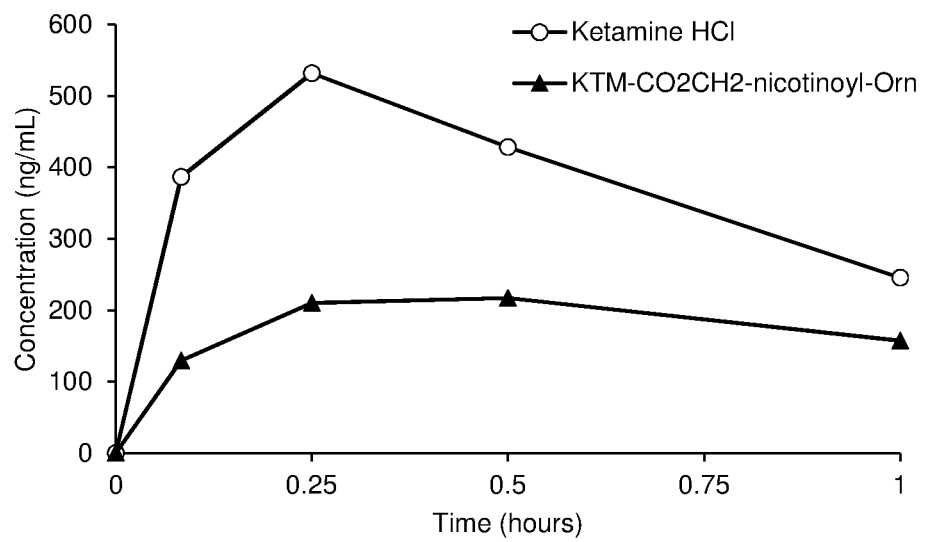
Figure 16A:
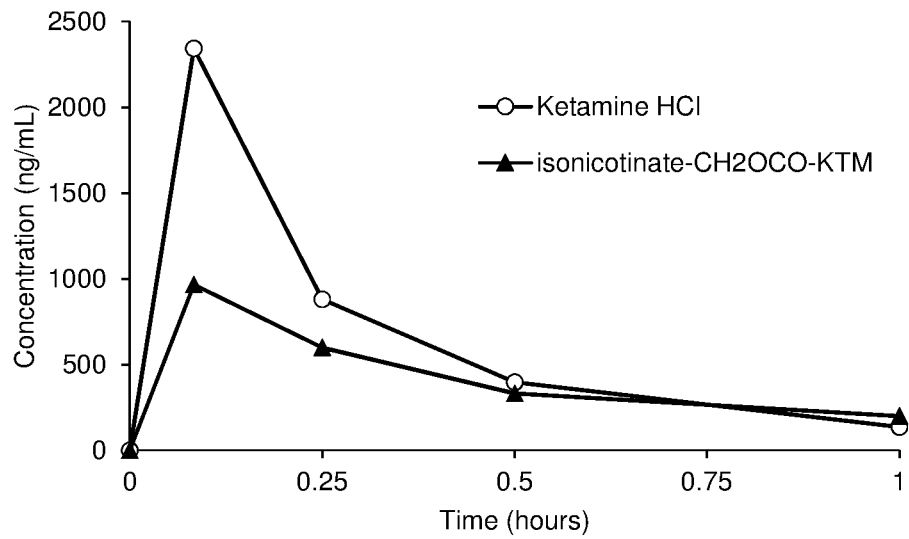
FIGS. 16A and 16B depict intranasal plasma concentration-time profiles of unconjugated ketamine as compared to isonicotinate-CH$_2$OCO-KTM.
Figure 16B:
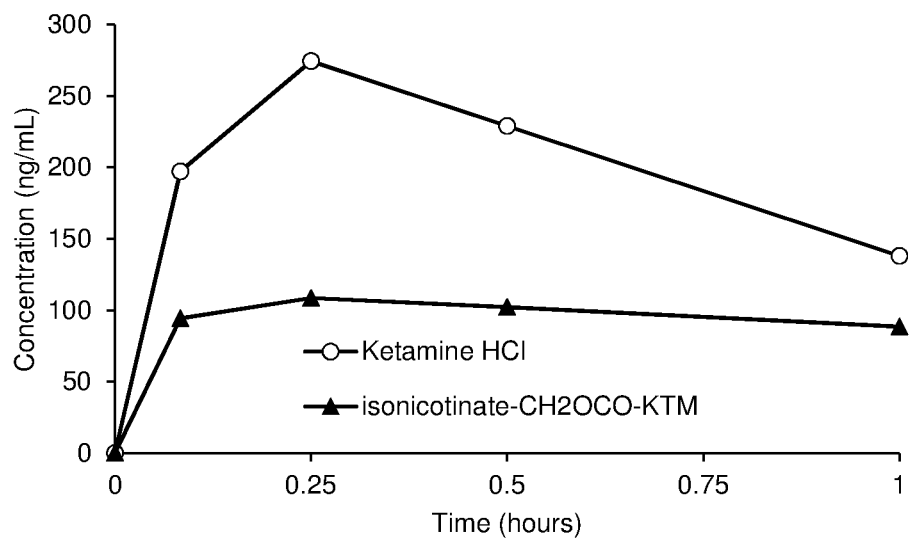
Figure 17A:
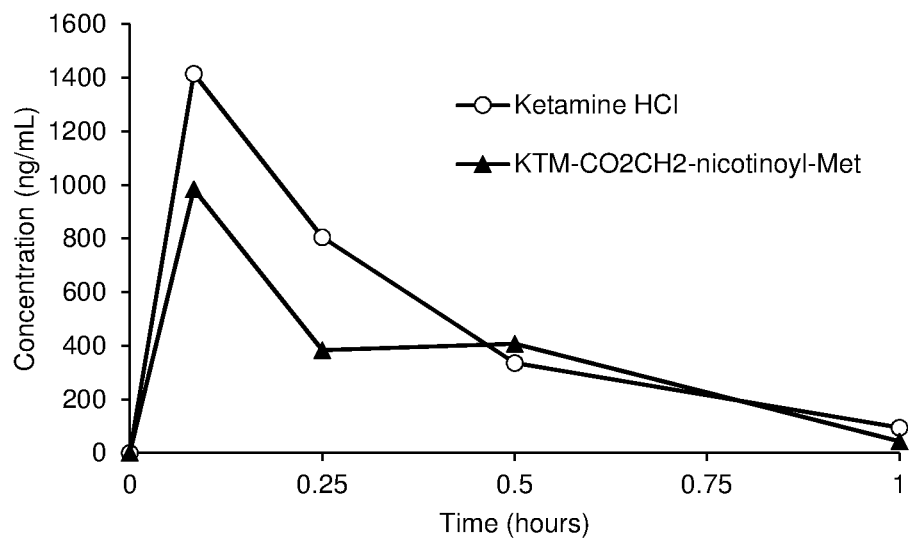
FIGS. 17A and 17B depict intranasal plasma concentration-time profiles of unconjugated ketamine as compared to KTM-CO$_2$CH$_2$-nicotinoyl-Met.
Figure 17B:
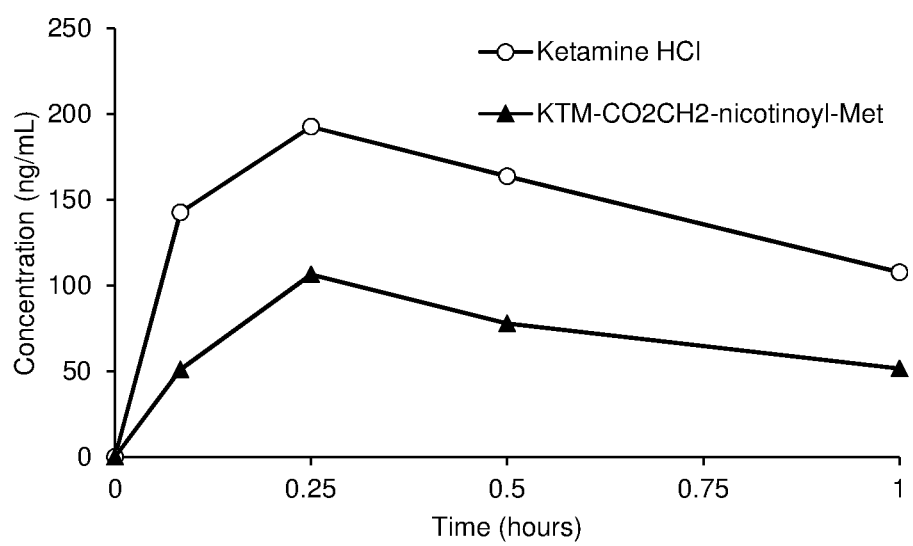
Figure 18A:
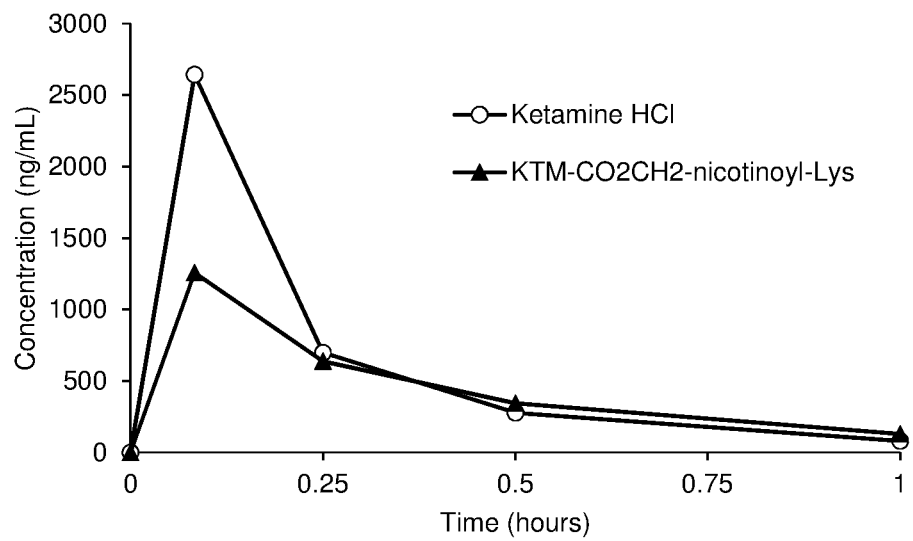
FIGS. 18A and 18B depict intranasal plasma concentration-time profiles of unconjugated ketamine as compared to KTM-CO$_2$CH$_2$-nicotinoyl-Lys.
Figure 18B:
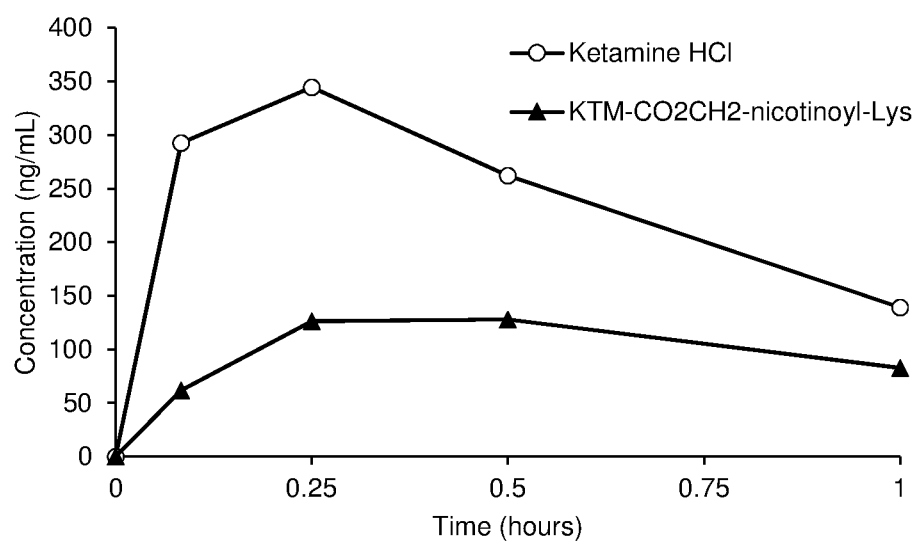
Figure 19A:
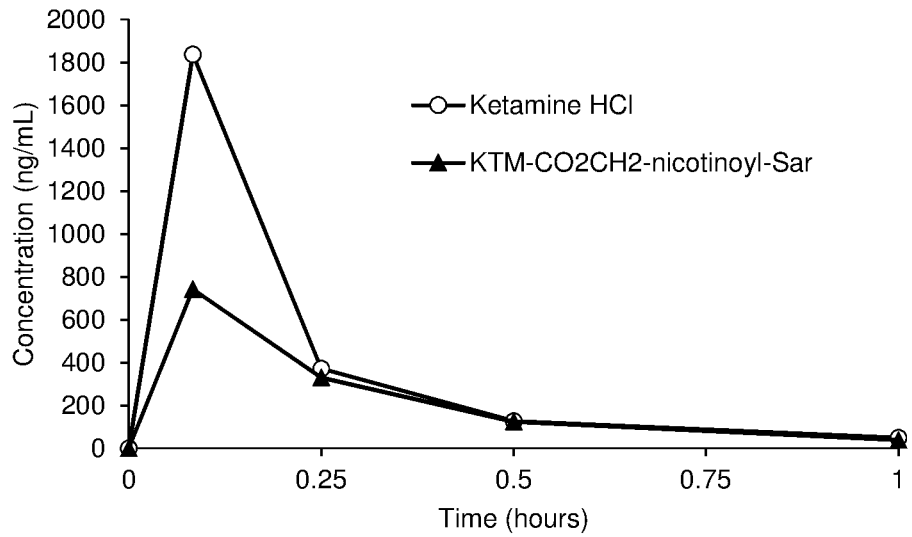
FIGS. 19A and 19B depict intranasal plasma concentration-time profiles of unconjugated ketamine as compared to KTM-CO$_2$CH$_2$-nicotinoyl-Sar.
Figure 19B:
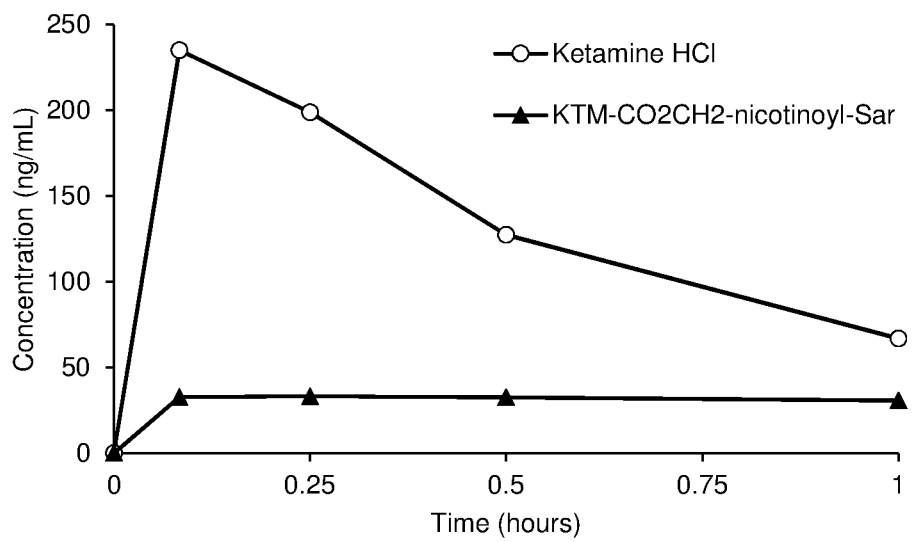
Figure 20A:
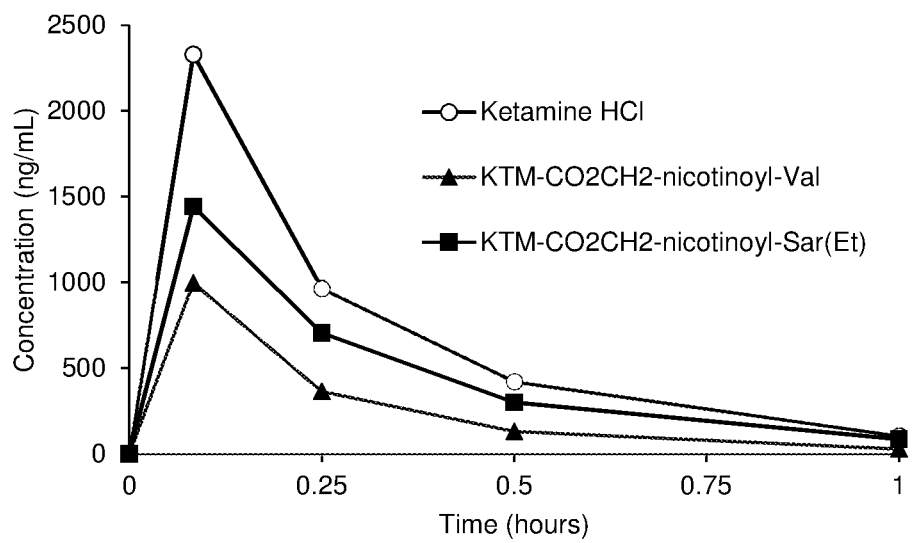
FIGS. 20A and 20B depict intranasal plasma concentration-time profiles of unconjugated ketamine as compared to KTM-CO$_2$CH$_2$-nicotinoyl-Val and KTM-CO$_2$CH$_2$-nicotinoyl-Sar(Et).
Figure 20B:
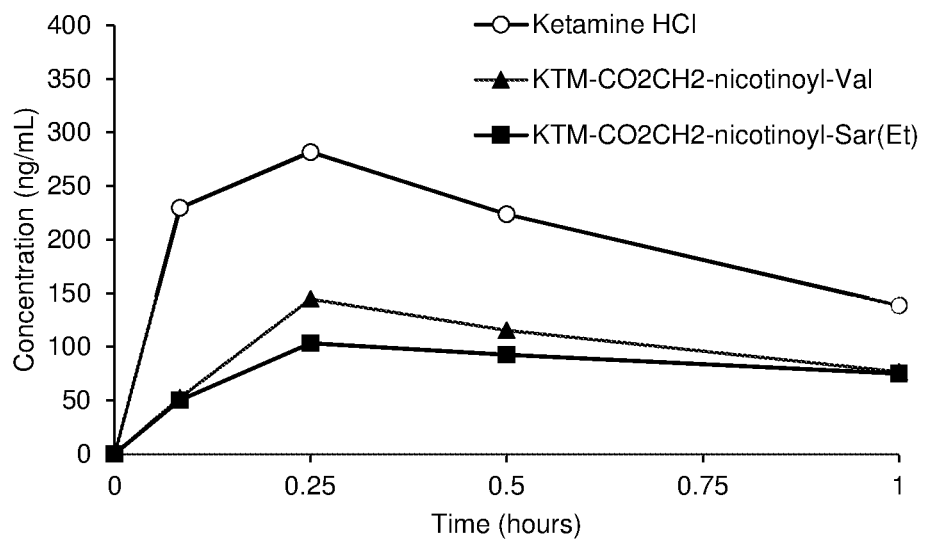
Figure 21A:
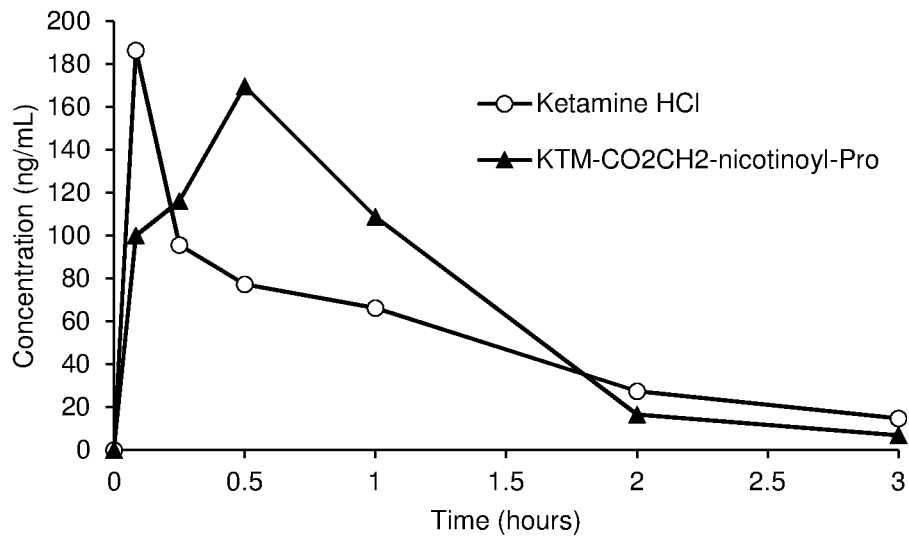
FIGS. 21A and 21B depict intravenous plasma concentration-time profiles of unconjugated ketamine as compared to KTM-CO$_2$CH$_2$-nicotinoyl-Pro.
Figure 21B:
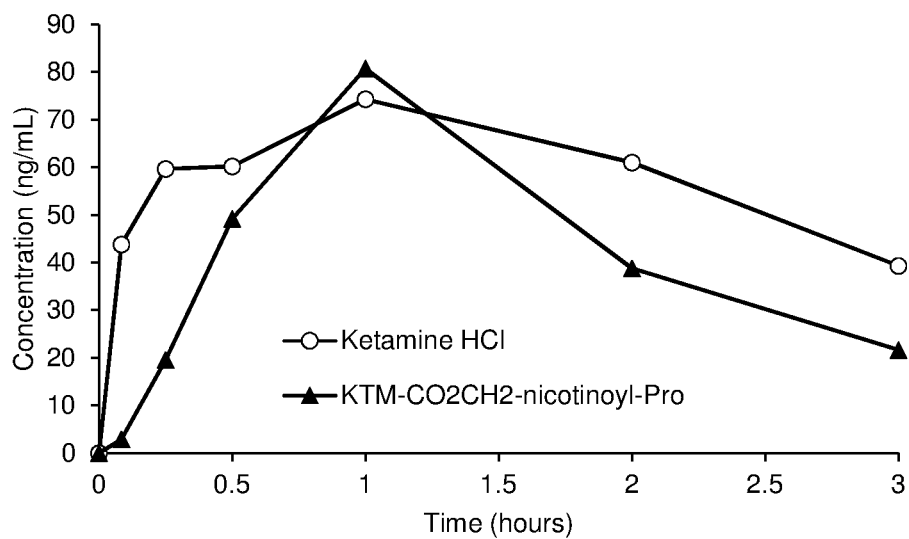
Figure 22A:
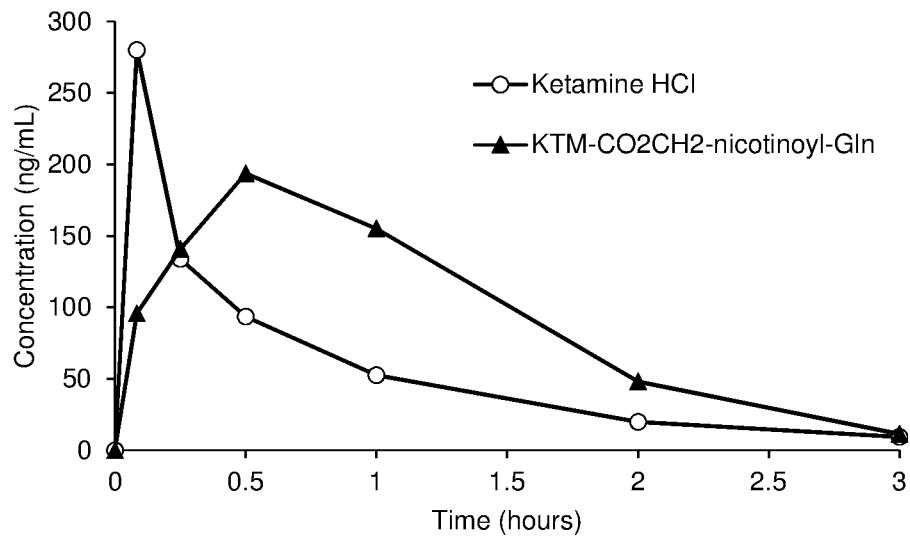
FIGS. 22A and 22B depict intravenous plasma concentration-time profiles of unconjugated ketamine as compared to KTM-CO$_2$CH$_2$-nicotinoyl-Gln.
Figure 22B:
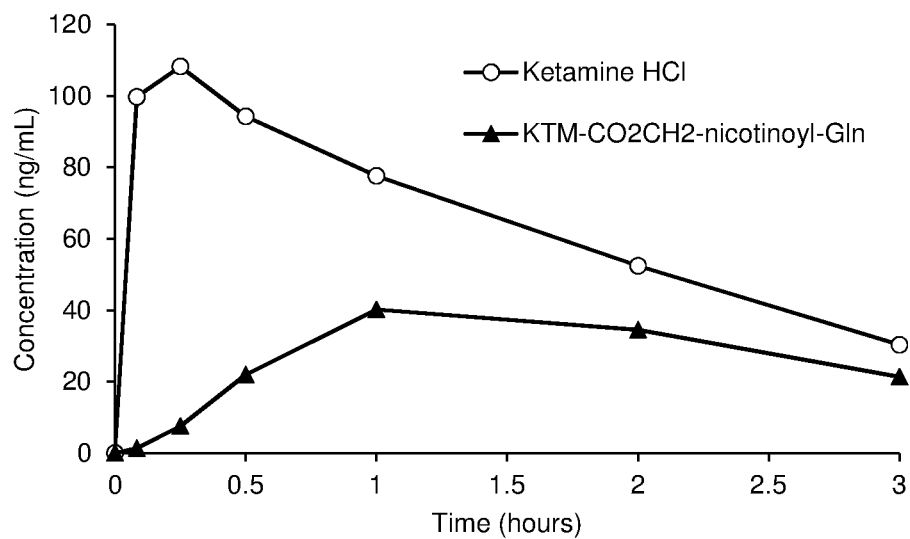

Oral plasma concentration-time profiles, intranasal plasma concentration-time profiles, and intravenous plasma concentration-time profiles of unconjugated ketamine as compared to various ketamine compounds are depicted in FIGS. 1A-22B. In some aspects, the ketamine compounds have increased oral bioavailability with respect to ketamine exposure when compared to unconjugated ketamine. Non-limiting examples of these ketamine compounds include KTM-$CO_2CH_2$-nicotinoyl-Ile, KTM-$CO_2CH_2$-nicotinoyl-Pro, KTM-$CO_2CH_2$-nicotinoyl-Val, and KTM-$CO_2CH_2$-nicotinoyl-Sar(Et).

In some aspects, the ketamine compounds have reduced norketamine exposure relative to ketamine exposure when compared to unconjugated ketamine. Non-limiting examples of these ketamine compounds include KTM-$CO_2CH_2$-nicotinoyl-Val, KTM-$CO_2CH_2$-nicotinoyl-Sar(Et), KTM-$CO_2CH_2$-nicotinoyl-Gln, KTM-$CO_2CH_2$-nicotinoyl-Met, isonicotinate-$CH_2OCO$-KTM, KTM-$CO_2CH_2$-nicotinoyl-Ile, KTM-$CO_2CH_2$-nicotinoyl-Pro, (S)-KTM-$CO_2CH_2$-nicotinoyl-Val, and KTM-$CO_2CH_2$-isonicotinoyl-Sar.

In some aspects, the ketamine compounds have reduced intranasal bioavailability of ketamine compared to unconjugated ketamine when administered intranasally. Non-limiting examples of these ketamine compounds include KTM-$CO_2CH_2$-nicotinoyl-Val, KTM-$CO_2CH_2$-nicotinoyl-Pro, KTM-$CO_2CH_2$-nicotinoyl-Sar(Et), KTM-$CO_2CH_2$-nicotinoyl-Gln, KTM-$CO_2CH_2$-nicotinoyl-Sar, isonicotinate-$CH_2OCO$-KTM, KTM-$CO_2CH_2$-nicotinoyl-Orn, KTM-$CO_2CH_2$-nicotinoyl-Met, and KTM-$CO_2CH_2$-nicotinoyl-Lys.

In some aspects, the ketamine compounds have reduced intravenous bioavailability of ketamine compared to unconjugated ketamine when administered intravenously. Non-limiting examples of these ketamine compounds include KTM-$CO_2CH_2$-nicotinoyl-Gln and KTM-$CO_2CH_2$-nicotinoyl-Pro.

In some aspects, the ketamine compounds provide an extended or delayed release of ketamine compared to unconjugated ketamine when administered orally. Non-limiting examples of these ketamine compounds include KTM-$CO_2CH_2$-nicotinoyl-Lys and KTM-$CO_2CH_2$-isonicotinoyl-Sar.

Synthetic Schemes

The presently described technology and its advantages will be better understood by reference to the following synthetic schemes. These schemes are provided to describe specific aspects of the present technology. By providing these specific schemes, the applicants do not limit the scope and spirit of the present technology.

1. Nicotinate-CH$_2$OCO-KTM HCl 3a and Isonicotinate-CH$_2$OCO-KTM HCl 3b:

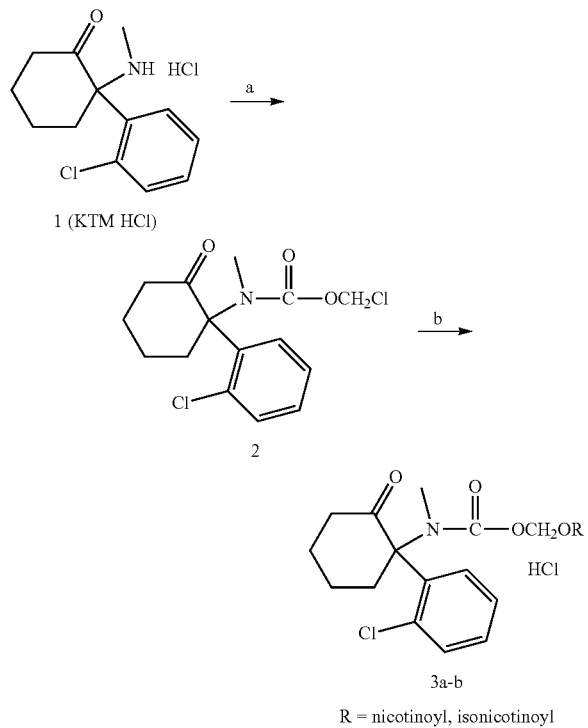

R = nicotinoyl, isonicotinoyl
(a) ClCH$_2$COCl, DIPEA, DCM; (b) ROAg, toluene, reflux, then HCl Synthesis of ClCH$_2$OCO-KTM 2:

Ketamine hydrochloride (KTM HCl, 1.371 g, 5 mmol) in DCM (35 mL) was cooled in an ice-water bath. DIPEA (2.09 mL, 12 mmol) was added, and the resulting mixture was stirred for 5 min. Then chloromethyl chloroformate (0.838 g, 6.5 mmol) in DCM (5 mL) was added over 8 min. The reaction was stirred at 0-10° C. for 40 min. and 5% of aq. NH$_4$Cl (20 mL) was added to quench the reaction. DCM layer was dried over sodium sulfate. The solvent was evaporated, and the residue was purified by silica gel chromatography column (hexanes:ethyl acetate, 3:1) to give 740 mg of 2 as syrup, which solidified when stored in a freezer. The yield was 44.8%.

Synthesis of Nicotinate-CH$_2$OCO-KTM HCl 3a:

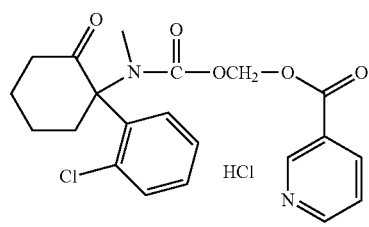

ClCH$_2$OCO-KTM 2 (0.330 g, 1 mmol) and silver nicotinate (0.276 g, 1.2 mmol) in toluene (20 mL) were refluxed for 4 hr. The solid was filtered off. The filtrate was concentrated, and the residue was purified by silica gel chromatography column (hexanes:ethyl acetate, 1.5:1 to 1:1.3) to give 0.20 g of an amorphous solid. To this solid was added 5 mL of DCM and treated with 1 M HCl/diethyl ether (1 mL). The solvent was evaporated, then dried over vacuum to give 0.206 g of 3a as an amorphous solid. The yield was 45%.

Synthesis of Isonicotinate-CH$_2$OCO-KTM HCl 3b:

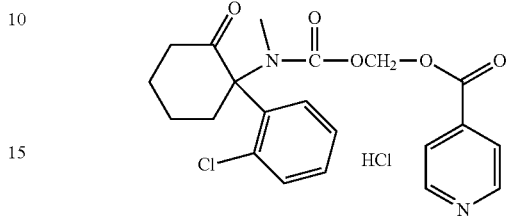

Isonicotinate-CH$_2$OCO-KTM HCl 3b was synthesized by a similar procedure as 3a. The yield was 26%.

Synthesis of Isonicotinate-CH$_2$OCO—(S)-KTM HCl S-3b and Isonicotinate-CH$_2$OCO—(R)-KTM HCl R-3b:

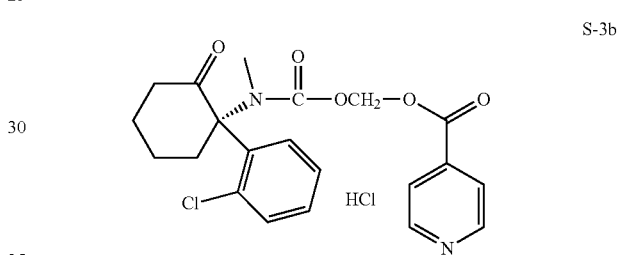

S-3b and R-3b were synthesized by similar procedures as 3a from S-Ketamine and R-Ketamine, respectively.

2. Phosphate-CH$_2$OCO-KTM 5:

Scheme 2

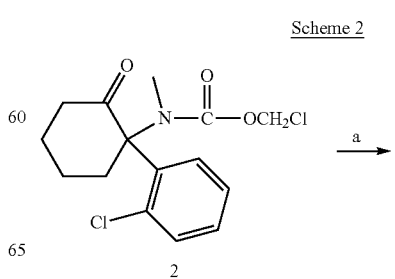

-continued

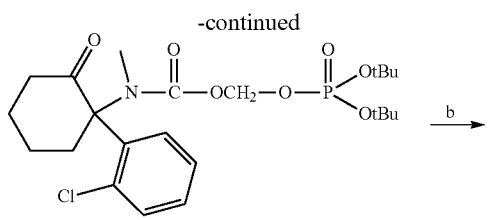

4

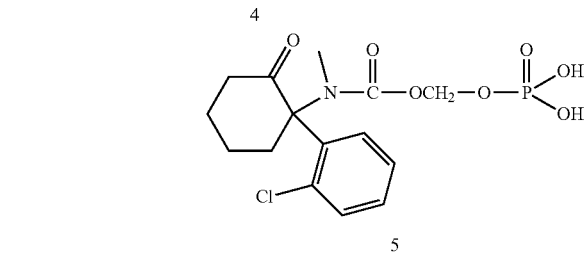

5

(a) (tBuO)₂P(O)OK, acetonitrile, reflux; (b) TFA, benzene 2.1 Synthesis of (tBuO)₂-phosphate-CH₂OCO-KTM 4:

ClCH₂OCO-KTM 2 (0.330 g, 1 mmol) and di-tert-butylphosphate potassium salt (0.621 g, 2.5 mmol) in acetonitrile (25 mL) were refluxed for 7 hr. The solid was filtered off and washed with acetonitrile (2×8 mL). The filtrate was concentrated, and the residue was purified by silica gel chromatography column (hexanes:ethyl acetate, 2.5:1 to 1:1) to give 0.210 g of 4 as syrup. The yield was 41.7%.

2.2 Synthesis of Phosphate-CH₂OCO-KTM 5:

To (tBuO)₂-phosphate-CH₂OCO-KTM 4 (200 mg) in benzene (8 mL) was added TFA (1 mL). The reaction was stirred at room temperature for 3 hr. Solvent was evaporated to dryness. To the residue was added DCM (2 mL) and hexanes (60 mL). The top layer was decanted after 1 hr. To the remaining residue in DCM (1.5 mL) was added TBME (50 mL). The top layer was decanted after 2 hr. The remaining solid was dried over vacuum to give 65 mg of 5. The yield was 41.8%.

3. Synthesis of KTM-CO₂CH₂—N-Me-morpholine 6:

Scheme 3

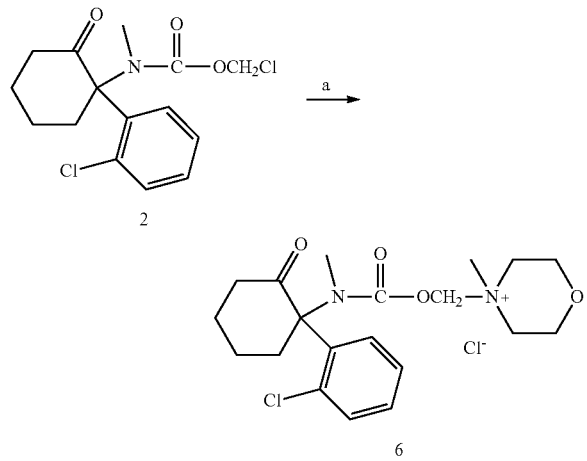

(a) N—Me-morpholine, acetonitrile, 80° C.

ClCH₂OCO-KTM 2 (0.231 g, 0.7 mmol) and N-Me-morpholine (0.496 g, 4.9 mmol) in acetonitrile (6 mL) were heated at 80° C. for 2 hr. Solvent was evaporated to give a solid that was recrystallized from DCM (8 mL). The mixture was kept overnight. Solids were collected, washed with DCM (1 mL×2), and dried over vacuum to give 205 mg of 6. The yield was 68%.

4. KTM-CO₂CH₂-Nicotinate 7a-d and KTM-CO₂CH₂-Isonicotinate 8a-b:

Scheme 4

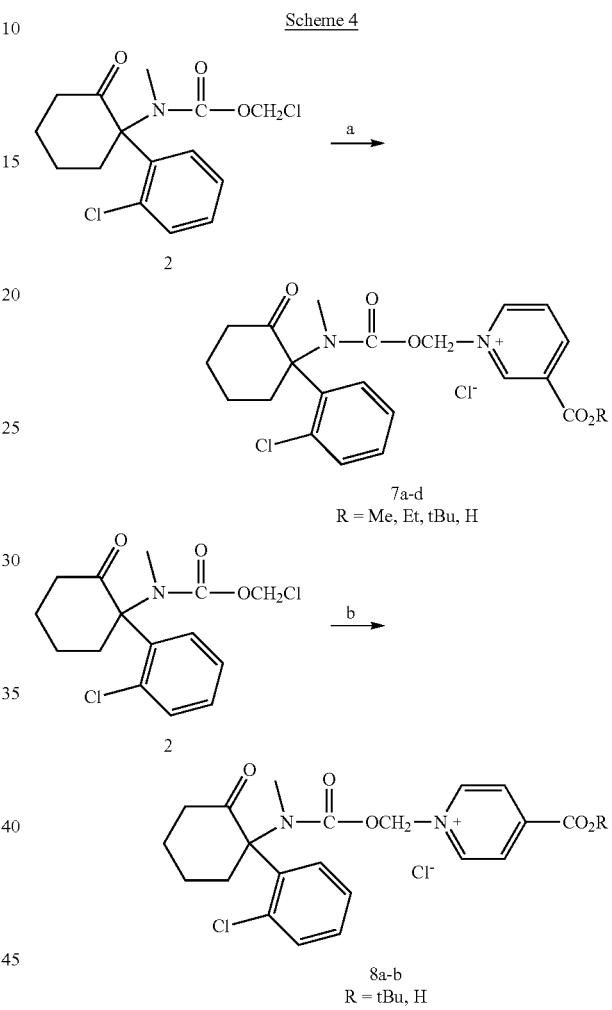

8a-b
R = tBu, H (a) nicotinate, NaI, Dowex 1x8; (b) isonicotinate, NaI, Dowex 1x8

4.1 Synthesis of KTM-CO₂CH₂-nicotinate(tBu) 7c:

ClCH₂OCO-KTM 2 (0.204 g, 0.618 mmol), tert-butyl nicotinate (0.108 g, 0.6 mmol) and NaI (90 mg, 0.6 mmol) in acetonitrile (8 mL) were heated at 80° C. for 1 hr. Solids were filtered off. The filtrate was concentrated to dryness and then dissolved in MeOH (8 mL). The solution was treated with Dowex 1×8 (200-400, 1.5 g). The filtrate was concentrated and dried over vacuum to give 290 mg of 7c as an amorphous solid. The yield was 95%.

4.2 Synthesis of KTM-CO₂CH₂-Nicotinate(Me) 7a

KTM-CO₂CH₂-nicotinate(Me) was prepared using a similar procedure as for 7c.

4.3 Synthesis of KTM-CO₂CH₂-Nicotinate(Et) 7b

KTM-CO₂CH₂-nicotinate(Et) was prepared using a similar procedure as for 7c.

4.4 Synthesis of KTM-CO₂CH₂-Nicotinate 7d

KTM-CO₂CH₂-nicotinate 7d was synthesized by treatment of 7c with 4M HCl/dioxane.

4.5 Synthesis of KTM-CO₂CH₂-Isonicotinate(tBu) 8a

KTM-CO₂CH₂-isonicotinate(tBu) was prepared using a similar procedure as for 7c.

4.6 Synthesis of KTM-CO₂CH₂-Isonicotinate(Me) 8b

KTM-CO₂CH₂-isonicotinate was prepared using a similar procedure as for 7d.

4.7 Synthesis of (S)-KTM-CO₂CH₂-Nicotinate S-7d and (R)-KTM-CO₂CH₂-Nicotinate R-7d (S)-KTM-CO₂CH₂-nicotinate and (R)-KTM-CO₂CH₂-nicotinate were prepared using the same procedure as for 7d.

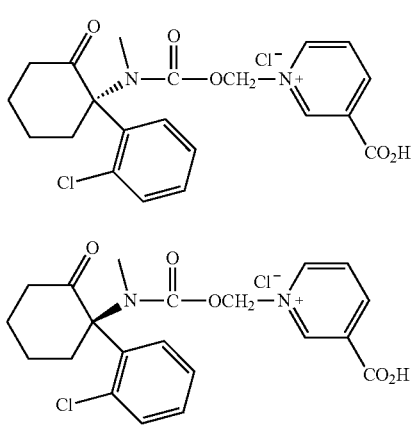

5. KTM-CO₂CH₂-Nicotinamide Conjugates 9a-h:

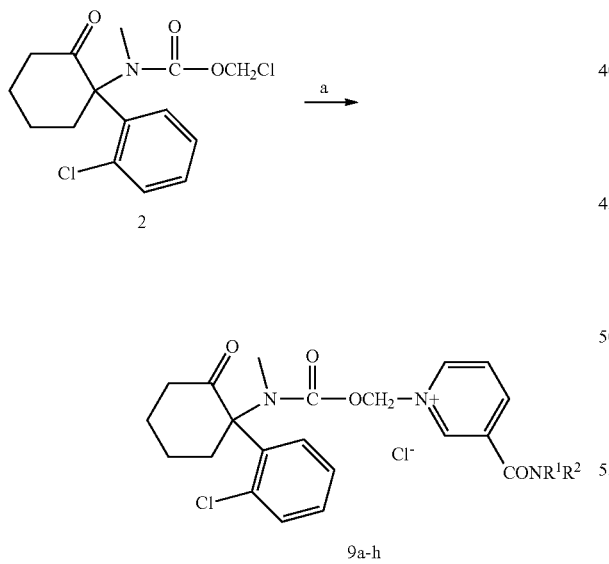

9a-h

NR¹R² = NH₂; NHCH₂CO₂Et; NMe₂; NMe(OMe); NMe(OBz); NMe(CH₂CO₂Et);

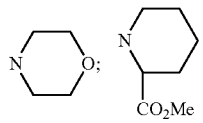

(a) nicotinamide, NaI, Dowex 1x8

5.1 General Procedure for the Syntheses of Conjugates 9a-h:

Nicotinamide (1 mmol), ClCH₂OCO-KTM 2 (1.03 mmol), and NaI (1 mmol) in acetonitrile (10 mL) were heated at 80° C. for 1 hr. The solid was filtered off. The filtrate was concentrated to dryness and then dissolved in MeOH (8 mL). The solution was treated with Dowex 1x8 (200-400, 2.5 g). The filtrate was concentrated and dried over vacuum to give 9a-h as an amorphous solid. The yield was 47-96%.

5.2 Synthesis of (S)-KTM-CO₂CH₂-Nicotinoyl-N-(Me)CH₂CO₂Et S-9b and (R)-KTM-CO₂CH₂-Nicotinoyl-N-(Me)CH₂CO₂Et R-9b:

Isomers of conjugate 9b, S-9b and R-9b were synthesized by the general procedure described in 5.1.

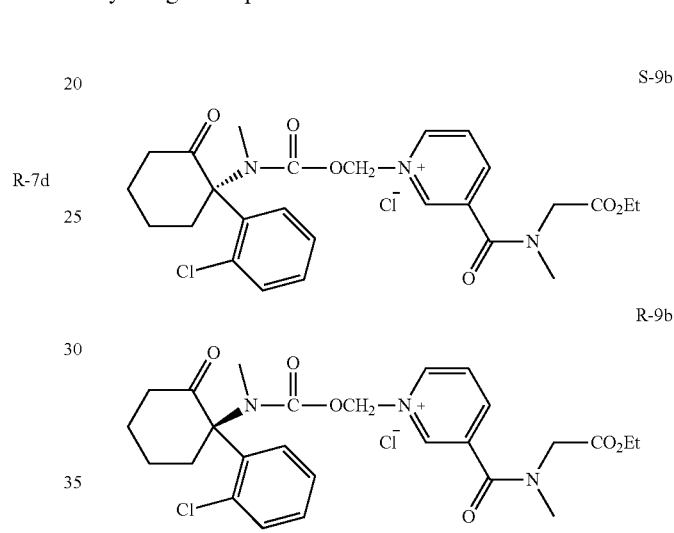

6. KTM-CO₂CH₂-Nicotinoyl-NR¹R² 10a-aa:

KTM-CO₂CH₂-Nicotinoyl-NR¹R², where HN—R¹R² is a standard, non-standard or synthetic amino acid, or peptide, was prepared according to Scheme 6.

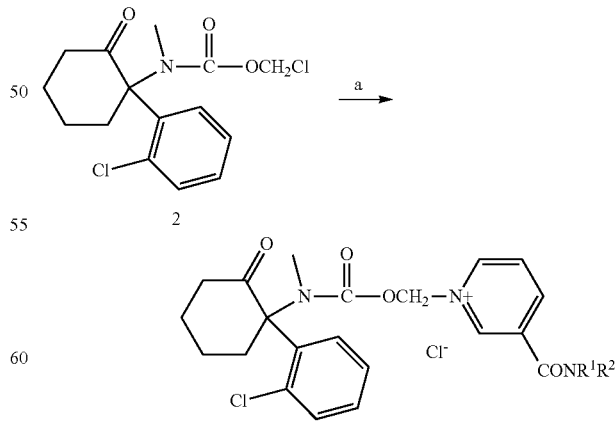

10a-aa (a) 1. Optionally protected HN—R¹R², NaI; 2. HCl or TFA, then Dowex 1x8

TABLE 1

Structures of conjugates 10a-aa

| Comp. | Structure |
|---|---|
| 10a | 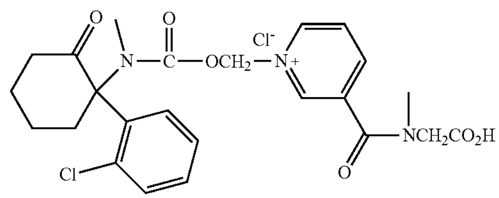 |
| 10b | 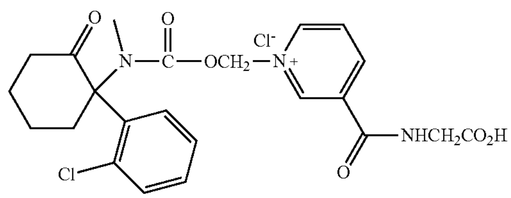 |
| 10c | 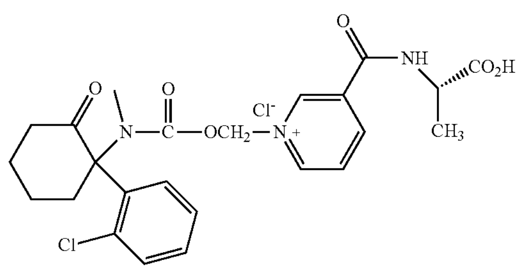 |
| 10d | 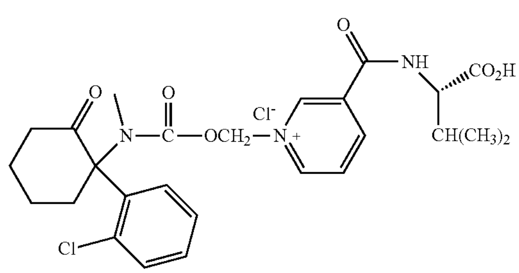 |
| 10e | 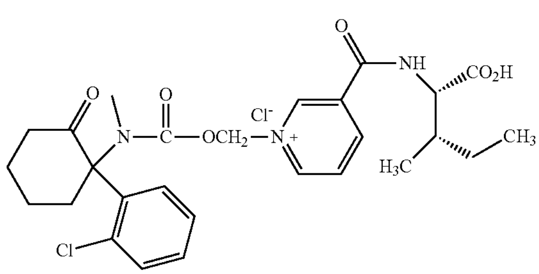 |
| 10f | 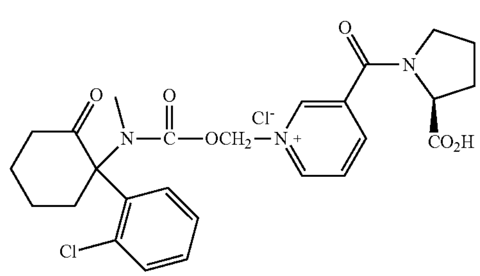 |

TABLE 1-continued

Structures of conjugates 10a-aa

| Comp. | Structure |
|---|---|
| 10g | 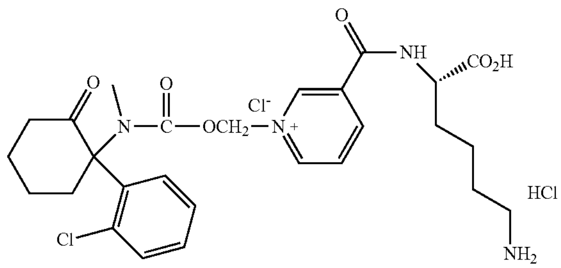 |
| 10h | 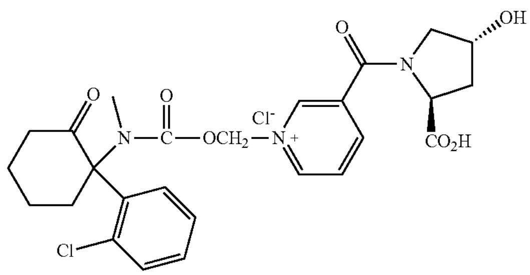 |
| 10i | 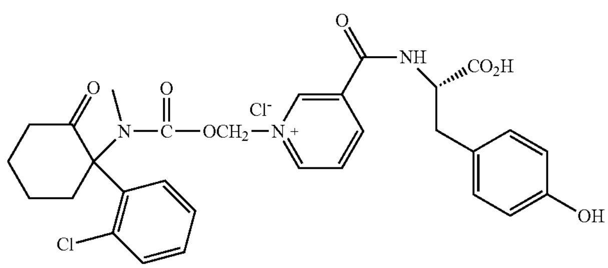 |
| 10j | 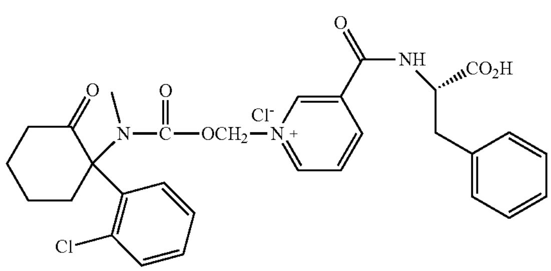 |
| 10k | 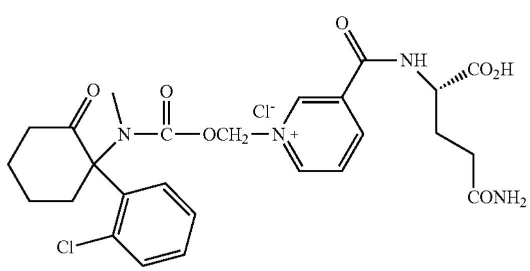 |

TABLE 1-continued

Structures of conjugates 10a-aa

| Comp. | Structure |
|---|---|
| 10l | 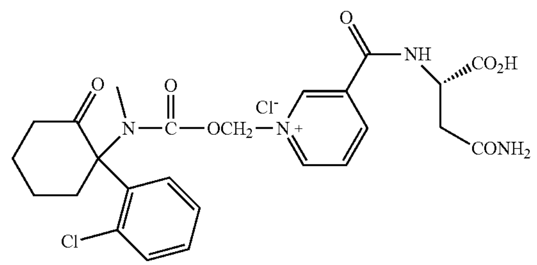 |
| 10m | 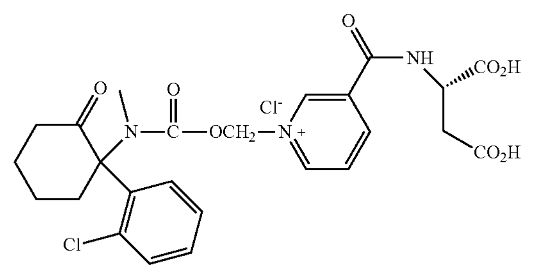 |
| 10n | 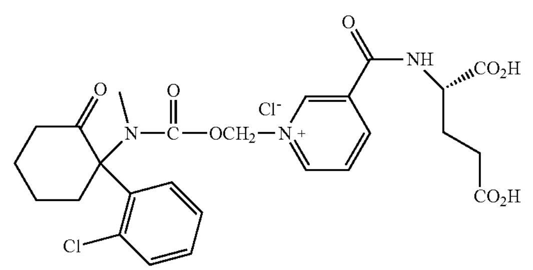 |
| 10o | 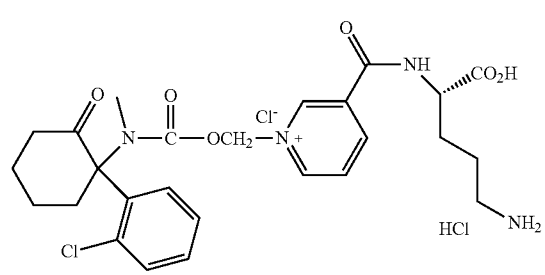 |
| 10p | 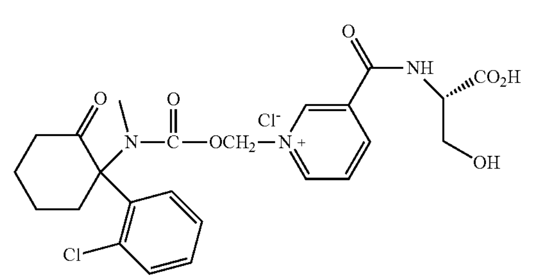 |

TABLE 1-continued
Structures of conjugates 10a-aa
| Comp. | Structure |
|---|---|
| 10q | 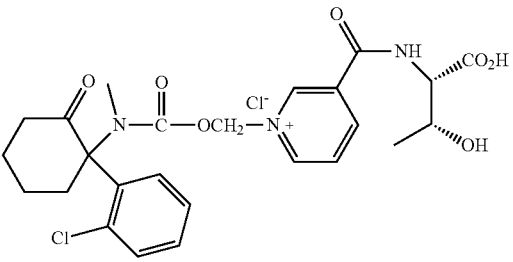 |
| 10r | 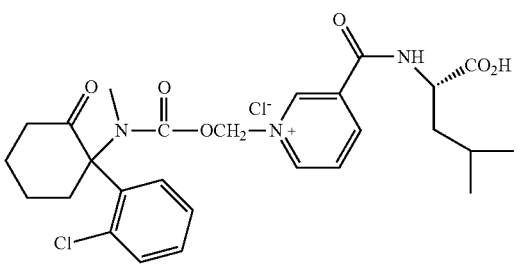 |
| 10s | 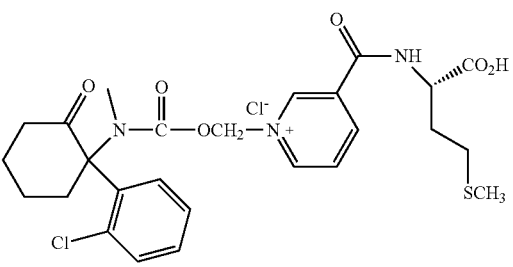 |
| 10t | 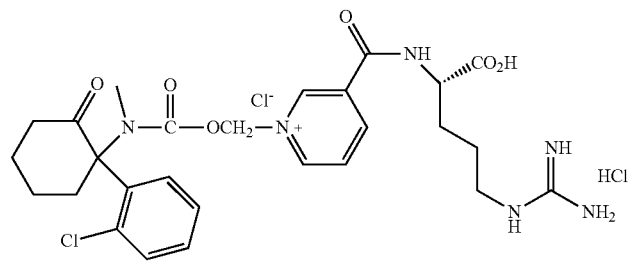 |
| 10u | 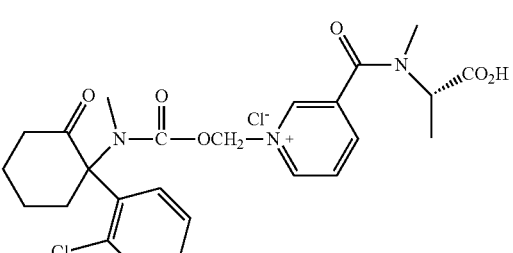 |

TABLE 1-continued
Structures of conjugates 10a-aa
| Comp. | Structure |
|---|---|
| 10v | 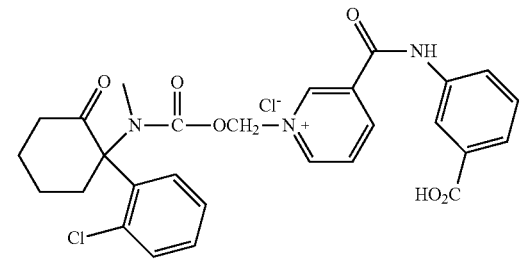 |
| 10w | 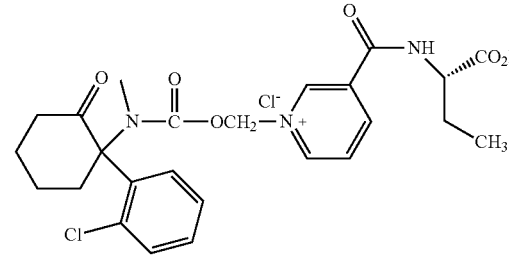 |
| 10x | 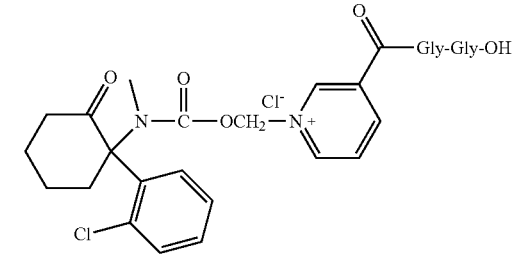 |
| 10y | 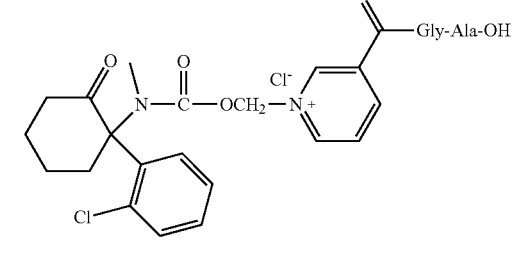 |
| 10z | 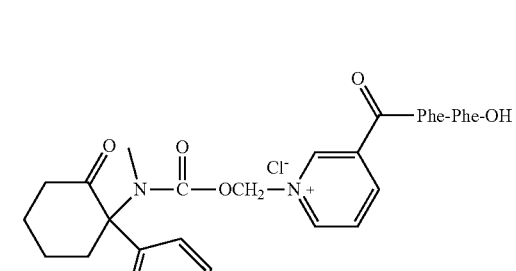 |

TABLE 1-continued

Structures of conjugates 10a-aa

| Comp. | Structure |
|---|---|
| 10aa | 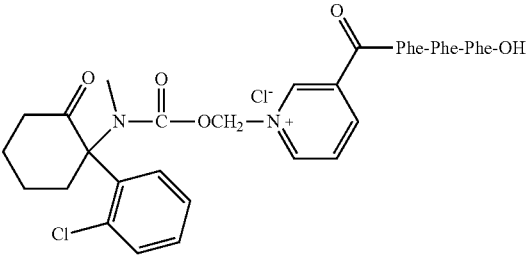 |

6.1 KTM-CO$_2$CH$_2$-Nicotinoyl-Sar-OH 10a:

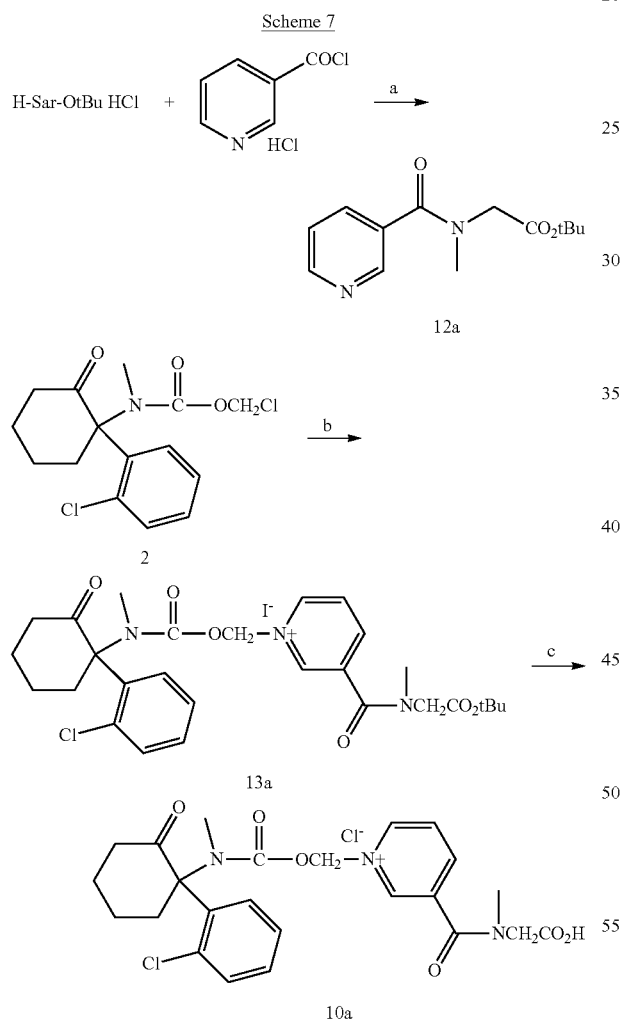

(a) TEA/DCM; (b) 12a, NaI, acetonitrile; (c) 4M HCl/dioxane, then Dowex 1x8

6.1.1 Synthesis of Nicotinoyl-Sar-OtBu 12a:

To sarcosine tert-butyl ester HCl (H-Sar-OtBu HCl, 0.545 g, 3 mmol) in DCM (30 mL) was added Et$_3$N (1.67 mL, 12 mmol). Subsequently, nicotinoyl chloride hydrochloride (0.561 g, 3.15 mmol) was added in 2 portions over 5 min under water bath (room temperature). The reaction was stirred for 1 hr. DCM was evaporated and the resulting residue dissolved in EtOAc (100 mL). The organic layer was washed with water, sat. NaHCO$_3$ and brine (20 mL each). The EtOAc layer was dried over Na$_2$SO$_4$. The product was purified by silica gel chromatography column (6% MeOH/DCM) to give 0.729 g of 12a as solid. The yield was 97%.

6.1.2 KTM-CO$_2$CH$_2$-Nicotinoyl-Sar-OH 10a:

Nicotinoyl-Sar(tBu)OtBu 12a (0.218 g, 0.87 mmol), ClCH$_2$OCO-KTM 2 (0.370 g, 1.12 mmol) and NaI (0.156 g, 1.04 mmol) in acetonitrile (10 mL) were heated at 80° C. for 1 hr. The solid was filtered off. The filtrate was concentrated and purified by silica gel chromatography column (9% MeOH/DCM) to give 588 mg of 13a as an amorphous solid. The solid in 4 M HCl/dioxane (10 mL) was stirred at room temperature for 4.5 hr. Solvent was evaporated to dryness, and the resulting residue dissolved in 10 mL of ethanol. The mixture was treated with Dowex 1x8 (200-400, Cl form, 1 g×2). The filtrate after resin treatment was concentrated and dried over vacuum. The resulting amorphous solid was dissolved in DCM (3 mL), and then TBME (40 mL) was added. The resulting solid was collected and dried over vacuum to give 450 mg of 10a. The yield was 86%.

6.1.3 Syntheses of KTM-CO$_2$CH$_2$-Nicotinoyl-NR$^1$R$^2$ 10b-aa:

10b-aa were synthesized using a similar procedure as for 10a.

6.1.4 Syntheses of S-10d, R-10d, S-10o, and R-10o:

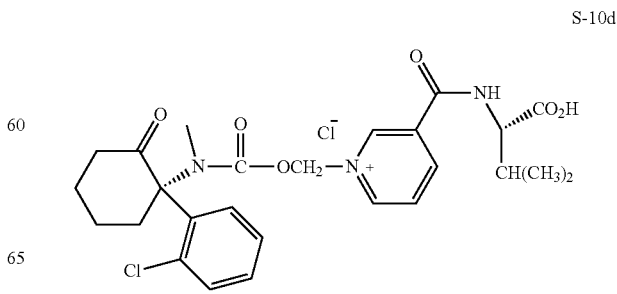

-continued

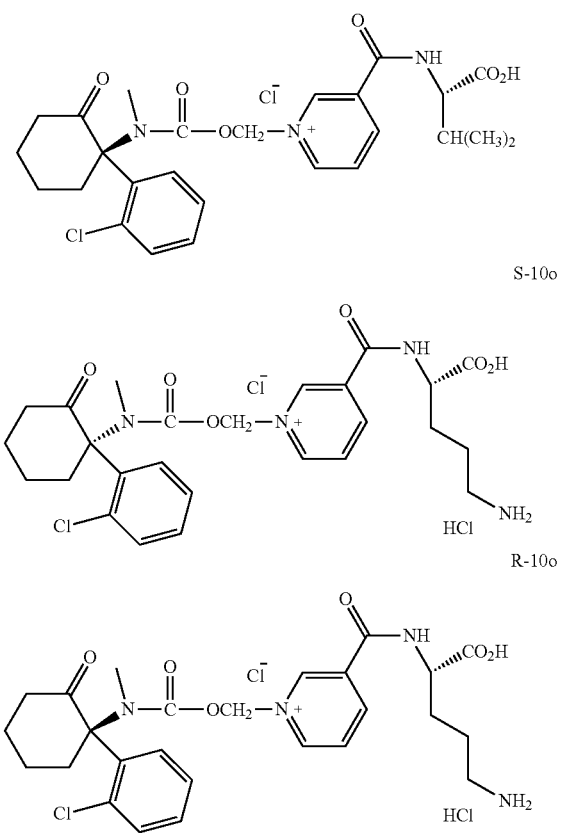

10d and 10o were synthesized using a similar procedure as for 10a. S-10d, R-10d, S-10o, and R-10o were synthesized by the same procedure as for 10d and 10o.

7. KTM-CO$_2$CH$_2$-Isonicotinoyl-NR$^1$R$^2$ 11a-f:

KTM-CO$_2$CH$_2$-isonicotinoyl-NR$^1$R$^2$, where HN—R$^1$R$^2$ is a standard, non-standard or synthetic amino acid, or peptide, was prepared according to Scheme 8.

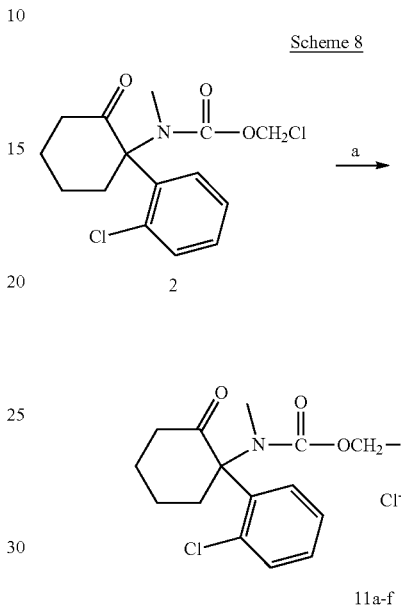

Scheme 8

(a) 1. Optionally protected HN—R$^1$R$^2$, NaI; 2. HCl, then Dowex 1x8

TABLE 2

Structures of conjugates 11a-f

| Comp. | Structure |
|---|---|
| 11a | 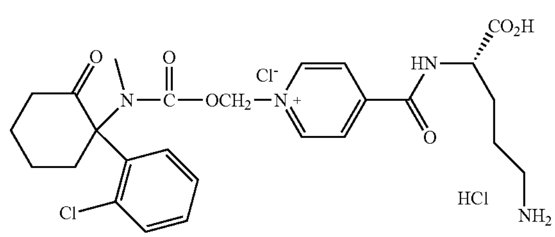 |
| 11b | 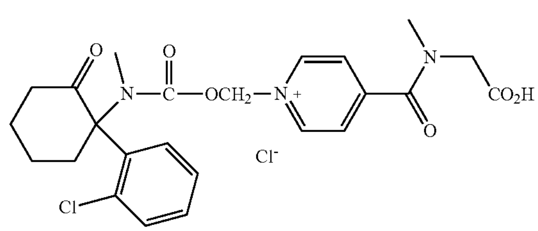 |

TABLE 2-continued
Structures of conjugates 11a-f
| Comp. | Structure |
|---|---|
| 11c | 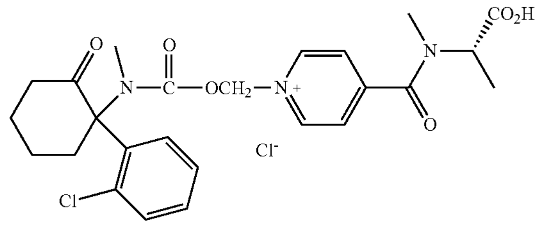 |
| 11d | 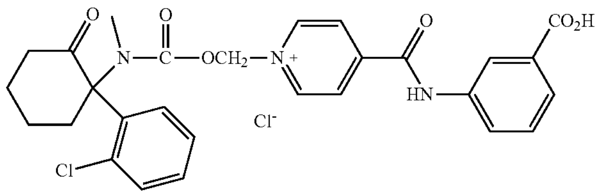 |
| 11e | 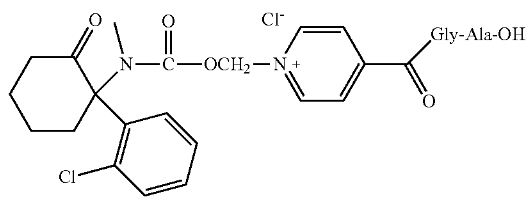 |
| 11f | 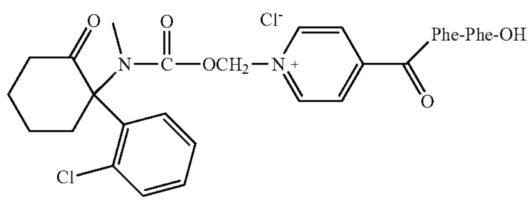 |
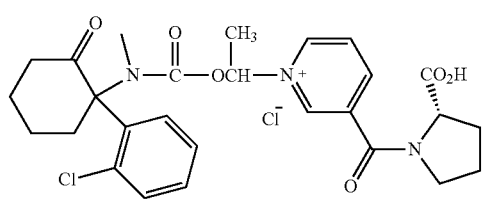
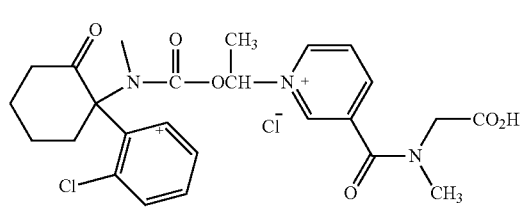
7.1 Syntheses of KTM-CO$_2$CH$_2$-Isonicotinoyl-NR$^1$R$^2$ 11a-f
11a-f were synthesized using a similar procedure as for 10a.
8. Conjugates 14a-b and 15:
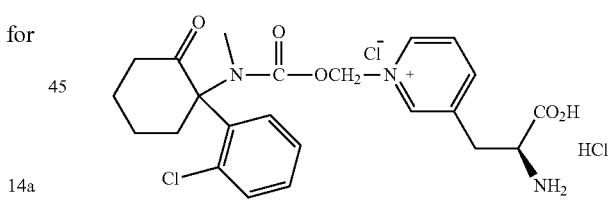
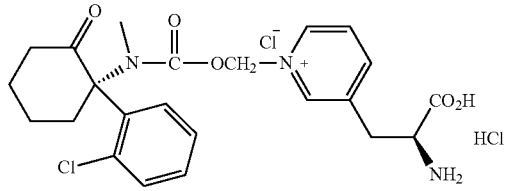
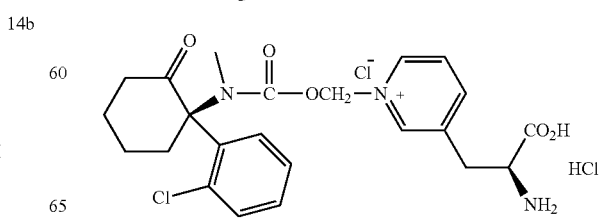

14a-b and 15 were synthesized using a similar procedure as for 10a. S-15 and R-15 were synthesized by the same procedure as for 15.

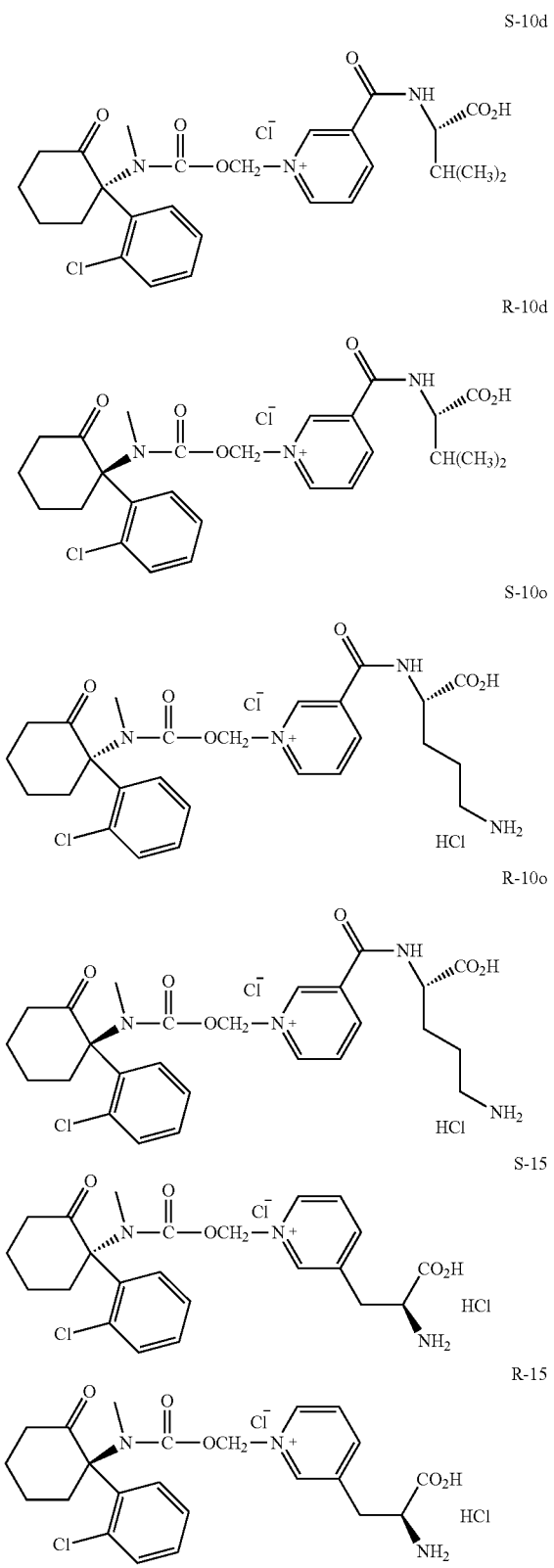

EXAMPLES

Pharmacokinetic Profiles of Ketamine Compounds

Studies were conducted in rats to assess the pharmacokinetics of various conjugated ketamine compounds when compared to ketamine HCl at the equivalent molar dose. Table 3 shows the mean pharmacokinetic parameters of ketamine in plasma after administration in Sprague-Dawley rats via oral gavage, and Table 4 shows the mean pharmacokinetic parameters of norketamine in plasma after administration in Sprague-Dawley rats via oral gavage. For both analyses, the blood was sampled at 0.25, 0.5, 1, 2, 3, and 4 hours post-dose of the ketamine compounds, and each ketamine compound had a molar equivalent to 4.64 mg/kg Ketamine HCl.

TABLE 3

Mean Pharmacokinetic Parameters of Ketamine in Plasma after Administration in Sprague-Dawley Rats via Oral Gavage.

| | Analyte = Ketamine | | |
| --- | --- | --- | --- |
| Ketamine Compound | $C_{max}$ (ng/mL) | $AUC_{0-4\,hr}$ (h*ng/mL) | $T_{max}$ (hours) |
| KTM-CO$_2$CH$_2$-nicotinoyl-Ala 10c | 16.9 | 23.2 | 1.00 |
| KTM-CO$_2$CH$_2$-nicotinoyl-Val 10d | 51.2 | 58.7 | 0.50 |
| KTM-CO$_2$CH$_2$-nicotinoyl-Sar 10a | 20.8 | 33.0 | 1.00 |
| KTM-CO$_2$CH$_2$-nicotinoyl-Ile 10e | 46.6 | 58.9 | 0.375 |
| KTM-CO$_2$CH$_2$-nicotinoyl-Pro 10f | 33.7 | 43.9 | 1.00 |
| KTM-CO$_2$CH$_2$-nicotinoyl-Lys 10g | 13.5 | 22.9 | 1.00 |
| KTM-CO$_2$CH$_2$-nicotinoyl-Gln 10k | 47.2 | 51.3 | 0.50 |
| KTM-CO$_2$CH$_2$-nicotinoyl-Orn 10o | 60.6 | 85.7 | 0.25 |
| KTM-CO$_2$CH$_2$-nicotinoyl-Met 10s | 32.7 | 39.5 | 1.00 |
| KTM-CO$_2$CH$_2$-nicotinoyl-Sar(Et) 9b | 23.1 | 37.8 | 1.00 |
| KTM-CO$_2$CH$_2$-isonicotinoyl-Sar 11b | 36.3 | 40.8 | 1.00 |
| KTM-CO$_2$CH$_2$-isonicotinoyl-N-Me-Ala 11c | 19.1 | 30.4 | 0.75 |
| (S)-KTM-CO$_2$CH$_2$-nicotinoyl-Sar(Et) S-9b | 16.7 | 28.2 | 1.00 |
| (S)-KTM-CO$_2$CH$_2$-nicotinoyl-Val S-10d | 33.3 | 32.9 | 0.50 |
| isonicotinate-CH$_2$OCO-KTM 3b | 35.7 | 55.2 | 0.25 |

TABLE 4

Mean Pharmacokinetic Parameters of Norketamine in Plasma afterAdministration in Sprague-Dawley Rats via Oral Gavage.

| | Analyte = Norketamine | | |
| --- | --- | --- | --- |
| Ketamine Compound | $C_{max}$ (ng/mL) | $AUC_{0-4\,hr}$ (h*ng/mL) | $T_{max}$ (hours) |
| KTM-CO$_2$CH$_2$-nicotinoyl-Ala 10c | 169 | 398 | 2.00 |
| KTM-CO$_2$CH$_2$-nicotinoyl-Val 10d | 162 | 406 | 2.00 |
| KTM-CO$_2$CH$_2$-nicotinoyl-Sar 10a | 229 | 492 | 2.00 |
| KTM-CO$_2$CH$_2$-nicotinoyl-Ile 10e | 586 | 971 | 1.00 |
| KTM-CO$_2$CH$_2$-nicotinoyl-Pro 10f | 509 | 792 | 1.00 |
| KTM-CO$_2$CH$_2$-nicotinoyl-Lys 10g | 203 | 429 | 1.50 |
| KTM-CO$_2$CH$_2$-nicotinoyl-Gln 10k | 232 | 480 | 2.00 |
| KTM-CO$_2$CH$_2$-nicotinoyl-Orn 10o | 365 | 615 | 2.00 |
| KTM-CO$_2$CH$_2$-nicotinoyl-Met 10s | 170 | 389 | 2.00 |
| KTM-CO$_2$CH$_2$-nicotinoyl-Sar(Et) 9b | 156 | 390 | 2.00 |
| KTM-CO$_2$CH$_2$-isonicotinoyl-Sar 11b | 238 | 404 | 1.00 |
| KTM-CO$_2$CH$_2$-isonicotinoyl-N-Me-Ala 11c | 134 | 231 | 1.00 |
| (S)-KTM-CO$_2$CH$_2$-nicotinoyl-Sar(Et) S-9b | 214 | 426 | 2.00 |
| (S)-KTM-CO$_2$CH$_2$-nicotinoyl-Val S-10d | 194 | 378 | 2.00 |
| isonicotinate-CH$_2$OCO-KTM 3b | 196 | 416 | 1.00 |

The pharmacokinetic data from these studies were used to also assess the relative oral bioavailability of ketamine (Table 5) and norketamine (Table 6) after administration of the ketamine compounds as compared to ketamine HCl in Sprague-Dawley rats. The calculated % parameter (i.e., % $C_{max}$ or % AUC) is equal to the mean conjugate PK parameter/mean comparator PK parameter.

TABLE 5

Relative Oral Bioavailability of Ketamine vs Study Comparator (Ketamine HCl) in Sprague-Dawley Rats.

| | Analyte = Ketamine | |
|---|---|---|
| Conjugate | % $C_{max}$ | % $AUC_{0-4\ hr}$ |
| KTM-CO$_2$CH$_2$-nicotinoyl-Ala 10c | 73.7% | 63.2% |
| KTM-CO$_2$CH$_2$-nicotinoyl-Val 10d | 223% | 160% |
| KTM-CO$_2$CH$_2$-nicotinoyl-Sar 10a | 112% | 93.9% |
| KTM-CO$_2$CH$_2$-nicotinoyl-Ile 10e | 246% | 223% |
| KTM-CO$_2$CH$_2$-nicotinoyl-Pro 10f | 178% | 166% |
| KTM-CO$_2$CH$_2$-nicotinoyl-Lys 10g | 71.2% | 75.4% |
| KTM-CO$_2$CH$_2$-nicotinoyl-Gln 10k | 110% | 97.0% |
| KTM-CO$_2$CH$_2$-nicotinoyl-Orn 10o | 138% | 98.5% |
| KTM-CO$_2$CH$_2$-nicotinoyl-Met 10s | 137% | 90.5% |
| KTM-CO$_2$CH$_2$-nicotinoyl-Sar(Et) 9b | 124% | 123% |
| KTM-CO$_2$CH$_2$-isonicotinoyl-Sar 11b | 90.7% | 99.8% |
| KTM-CO$_2$CH$_2$-isonicotinoyl-N-Me-Ala 11c | 127% | 119% |
| (S)-KTM-CO$_2$CH$_2$-nicotinoyl-Sar(Et) S-9b | 63.4% | 67.3% |
| (S)-KTM-CO$_2$CH$_2$-nicotinoyl-Val S-10d | 126% | 78.4% |
| isonicotinate-CH$_2$OCO-KTM 3b | 60.3% | 88.1% |

TABLE 6

Relative Oral Bioavailability of Norketamine vs Study Comparator (Ketamine HCl) in Sprague-Dawley Rats.

| | Analyte = Norketamine | |
|---|---|---|
| Conjugate | % $C_{max}$ | % $AUC_{0-4\ hr}$ |
| KTM-CO$_2$CH$_2$-nicotinoyl-Ala 10c | 54.9% | 59.0% |
| KTM-CO$_2$CH$_2$-nicotinoyl-Val 10d | 52.7% | 60.1% |
| KTM-CO$_2$CH$_2$-nicotinoyl-Sar 10a | 112% | 87.7% |
| KTM-CO$_2$CH$_2$-nicotinoyl-Ile 10e | 136% | 148% |
| KTM-CO$_2$CH$_2$-nicotinoyl-Pro 10f | 118% | 120% |
| KTM-CO$_2$CH$_2$-nicotinoyl-Lys 10g | 85.6% | 84.7% |
| KTM-CO$_2$CH$_2$-nicotinoyl-Gln 10k | 56.8% | 50.5% |
| KTM-CO$_2$CH$_2$-nicotinoyl-Orn 10o | 151% | 116% |
| KTM-CO$_2$CH$_2$-nicotinoyl-Met 10s | 37.8% | 51.6% |
| KTM-CO$_2$CH$_2$-nicotinoyl-Sar(Et) 9b | 66.9% | 62.7% |
| KTM-CO$_2$CH$_2$-isonicotinoyl-Sar 11b | 63.7% | 84.3% |
| KTM-CO$_2$CH$_2$-isonicotinoyl-N-Me-Ala 11c | 77.7% | 70.6% |
| (S)-KTM-CO$_2$CH$_2$-nicotinoyl-Sar(Et) S-9b | 63.8% | 69.0% |
| (S)-KTM-CO$_2$CH$_2$-nicotinoyl-Val S-10d | 57.8% | 61.4% |
| isonicotinate-CH$_2$OCO-KTM 3b | 44.6% | 56.5% |

For each ketamine compound, a relative % exposure ratio of ketamine and norketamine can be calculated for $C_{max}$ and AUC by dividing the respective relative oral bioavailability of ketamine by the relative oral bioavailability of norketamine (Table 7). A higher ratio indicates reduced norketamine exposure relative to ketamine exposure. As norketamine is a less potent antagonist at the NMDA receptor compared to ketamine, reduced norketamine exposure relative to ketamine exposure may increase the overall potency of the conjugated ketamine compounds. The increased potency may allow for reduced doses of the conjugated ketamine compounds on a molar basis with similar therapeutic effect when compared to unconjugated ketamine. The reduced doses of the conjugated ketamine compounds may improve the side effects or adverse reactions when compared to unconjugated ketamine.

TABLE 7

Relative % Exposure Ratios ($C_{max}$ and AUC) of Ketamine and Norketamine in Plasma after Administration in Sprague-Dawley Rats via Oral Gavage.

| | % Exposure Ratio Ketamine:Norketamine | |
|---|---|---|
| Conjugate | $C_{max}$ | $AUC_{0-4\ hr}$ |
| KTM-CO$_2$CH$_2$-nicotinoyl-Ala 10c | 1.34 | 1.07 |
| KTM-CO$_2$CH$_2$-nicotinoyl-Val 10d | 4.24 | 2.66 |
| KTM-CO$_2$CH$_2$-nicotinoyl-Sar 10a | 1.00 | 1.07 |
| KTM-CO$_2$CH$_2$-nicotinoyl-Ile 10e | 1.81 | 1.51 |
| KTM-CO$_2$CH$_2$-nicotinoyl-Pro 10f | 1.50 | 1.38 |
| KTM-CO$_2$CH$_2$-nicotinoyl-Lys 10g | 0.83 | 0.89 |
| KTM-CO$_2$CH$_2$-nicotinoyl-Gln 10k | 1.93 | 1.92 |
| KTM-CO$_2$CH$_2$-nicotinoyl-Orn 10o | 0.91 | 0.85 |
| KTM-CO$_2$CH$_2$-nicotinoyl-Met 10s | 3.63 | 1.76 |
| KTM-CO$_2$CH$_2$-nicotinoyl-Sar(Et) 9b | 1.85 | 1.96 |
| KTM-CO$_2$CH$_2$-isonicotinoyl-Sar 11b | 1.42 | 1.18 |
| KTM-CO$_2$CH$_2$-isonicotinoyl-N-Me-Ala 11c | 1.63 | 1.68 |
| (S)-KTM-CO$_2$CH$_2$-nicotinoyl-Sar(Et) S-9b | 0.99 | 0.97 |
| (S)-KTM-CO$_2$CH$_2$-nicotinoyl-Val S-10d | 2.19 | 1.28 |
| isonicotinate-CH$_2$OCO-KTM 3b | 1.35 | 1.56 |

Note:
% exposure ratio = ketamine % parameter/norketamine % parameter

The pharmacokinetics of ketamine (Table 8) and norketamine (Table 9) in plasmas after intranasal administration in rats were also assessed. The blood samples were taken at 0.0833, 0.25, 0.5, and 1 hours post-dose, and each dose was the molar equivalent to 2.32 mg/kg Ketamine HCL.

TABLE 8

Mean Pharmacokinetic Parameters of Ketamine in Plasma after Intranasal Administration in Sprague-Dawley Rats.

| | Analyte = Ketamine | | |
|---|---|---|---|
| Conjugate | $C_{max}$ (ng/mL) | $AUC_{0-1\ hr}$ (h*ng/mL) | $T_{max}$ (hours) |
| KTM-CO$_2$CH$_2$-nicotinoyl-Pro 10f | 1791 | 527 | 0.083 |
| KTM-CO$_2$CH$_2$-nicotinoyl-Gln 10k[a] | 1763 | 430 | 0.083 |
| KTM-CO$_2$CH$_2$-nicotinoyl-Orn 10o | 2235 | 648 | 0.083 |
| isonicotinate-CH$_2$OCO-KTM 3b | 965 | 428 | 0.083 |
| KTM-CO$_2$CH$_2$-nicotinoyl-Met 10s | 1109 | 366 | 0.083 |
| KTM-CO$_2$CH$_2$-nicotinoyl-Lys 10g | 1257 | 410 | 0.083 |
| KTM-CO$_2$CH$_2$-nicotinoyl-Sar 10a | 742 | 217 | 0.083 |
| KTM-CO$_2$CH$_2$-nicotinoyl-Val 10d | 997 | 257 | 0.083 |
| KTM-CO$_2$CH$_2$-nicotinoyl-Sar(Et) 9b | 1443 | 461 | 0.083 |

[a]Time course stopped at 0.5 hours

TABLE 9

Mean Pharmacokinetic Parameters of Norketamine in Plasma after Intranasal Administration in Sprague-Dawley Rats.

| | Analyte = Norketamine | | |
|---|---|---|---|
| Conjugate | $C_{max}$ (ng/mL) | $AUC_{0-1\ hr}$ (h*ng/mL) | $T_{max}$ (hours) |
| KTM-CO$_2$CH$_2$-nicotinoyl-Pro 10f | 240 | 190 | 0.25 |
| KTM-CO$_2$CH$_2$-nicotinoyl-Gln 10k[a] | 200 | 76.4 | 0.50 |
| KTM-CO$_2$CH$_2$-nicotinoyl-Orn 10o | 220 | 170 | 0.50 |
| isonicotinate-CH$_2$OCO-KTM 3b | 110 | 96.2 | 0.25 |
| KTM-CO$_2$CH$_2$-nicotinoyl-Met 10s | 106 | 70.7 | 0.25 |
| KTM-CO$_2$CH$_2$-nicotinoyl-Lys 10g | 137 | 93.0 | 0.50 |
| KTM-CO$_2$CH$_2$-nicotinoyl-Sar 10a | 36.7 | 30.9 | 0.375 |
| KTM-CO$_2$CH$_2$-nicotinoyl-Val 10d | 144 | 99.0 | 0.25 |
| KTM-CO$_2$CH$_2$-nicotinoyl-Sar(Et) 9b | 105 | 81.3 | 0.25 |

[a]Time course stopped at 0.5 hours

The pharmacokinetic data from these studies were used to also assess the relative intranasal bioavailability of ketamine (Table 10) and norketamine (Table 11) of the ketamine compounds as compared to ketamine HCl in Sprague-Dawley rats. The calculated % parameter (i.e., % $C_{max}$ or % AUC) is equal to the mean conjugate PK parameter/mean comparator PK parameter.

TABLE 10

Relative Intranasal Bioavailability of Ketamine vs Study Comparator (Ketamine HCl) in Sprague-Dawley Rats.

| | Analyte = Ketamine | |
|---|---|---|
| Conjugate | % $C_{max}$ | % $AUC_{0-1\,hr}$ |
| KTM-CO$_2$CH$_2$-nicotinoyl-Pro 10f | 61.3% | 63.6% |
| KTM-CO$_2$CH$_2$-nicotinoyl-Gln 10k[a] | 69.5% | 55.9% |
| KTM-CO$_2$CH$_2$-nicotinoyl-Orn 10o | 73.5% | 72.9% |
| isonicotinate-CH$_2$OCO-KTM 3b | 41.2% | 64.7% |
| KTM-CO$_2$CH$_2$-nicotinoyl-Met 10s | 78.3% | 74.1% |
| KTM-CO$_2$CH$_2$-nicotinoyl-Lys 10g | 47.5% | 68.4% |
| KTM-CO$_2$CH$_2$-nicotinoyl-Sar 10a | 40.4% | 59.2% |
| KTM-CO$_2$CH$_2$-nicotinoyl-Val 10d | 42.8% | 37.9% |
| KTM-CO$_2$CH$_2$-nicotinoyl-Sar(Et) 9b | 62.0% | 68.1% |

Note:
% parameter = mean conjugate parameter/mean comparator parameter
[a]Time course stopped at 0.5 hours

TABLE 11

Relative Intranasal Bioavailability of Norketamine vs Study Comparator (Ketamine HCl) in Sprague-Dawley Rats.

| | Analyte = Norketamine | |
|---|---|---|
| Conjugate | % $C_{max}$ | % $AUC_{0-1\,hr}$ |
| KTM-CO$_2$CH$_2$-nicotinoyl-Pro 10f | 43.7% | 49.6% |
| KTM-CO$_2$CH$_2$-nicotinoyl-Gln 10k[a] | 40.6% | 20.4% |
| KTM-CO$_2$CH$_2$-nicotinoyl-Orn 10o | 41.4% | 43.9% |
| isonicotinate-CH$_2$OCO-KTM 3b | 40.2% | 48.4% |
| KTM-CO$_2$CH$_2$-nicotinoyl-Met 10s | 55.3% | 48.3% |
| KTM-CO$_2$CH$_2$-nicotinoyl-Lys 10g | 39.2% | 38.5% |
| KTM-CO$_2$CH$_2$-nicotinoyl-Sar 10a | 15.5% | 22.8% |
| KTM-CO$_2$CH$_2$-nicotinoyl-Val 10d | 51.3% | 48.1% |
| KTM-CO$_2$CH$_2$-nicotinoyl-Sar(Et) 9b | 37.1% | 39.5% |

Note:
% parameter = mean conjugate parameter/mean comparator parameter
[a]Time course stopped at 0.5 hours For each ketamine compound, a relative % exposure ratio of ketamine after oral and intranasal administration can be calculated for $C_{max}$ and AUC by dividing the respective relative oral bioavailability of ketamine by the relative intranasal bioavailability of ketamine (Table 12). A higher ratio indicates that the conjugated ketamine compound has reduced intranasal exposure compared to unconjugated ketamine when the conjugated and unconjugated ketamine compound are administered at doses that are therapeutically equivalent via the oral route. This reduced intranasal exposure shows that the conjugated ketamine compound has reduced intranasal abuse potential or is resistant to intranasal abuse when compared to unconjugated ketamine.

TABLE 12

Relative % Exposure Ratios ($C_{max}$ and AUC) of Ketamine after Oral (PO) and Intranasal (IN) Administration in Sprague-Dawley Rats via Oral Gavage.

| | % Exposure Ratio PO:IN | |
|---|---|---|
| Conjugate | $C_{max}$ | AUC |
| KTM-CO$_2$CH$_2$-nicotinoyl-Val 10d | 5.22 | 4.22 |
| KTM-CO$_2$CH$_2$-nicotinoyl-Sar 10a | 2.78 | 1.59 |
| KTM-CO$_2$CH$_2$-nicotinoyl-Pro 10f | 2.90 | 2.61 |
| KTM-CO$_2$CH$_2$-nicotinoyl-Lys 10g | 1.50 | 1.10 |
| KTM-CO$_2$CH$_2$-nicotinoyl-Gln 10k | 1.58 | 1.74 |
| KTM-CO$_2$CH$_2$-nicotinoyl-Orn 10o | 1.88 | 1.35 |
| KTM-CO$_2$CH$_2$-nicotinoyl-Met 10s | 1.75 | 1.22 |
| KTM-CO$_2$CH$_2$-nicotinoyl-Sar(Et) 9b | 2.00 | 1.80 |
| isonicotinate-CH$_2$OCO-KTM 3b | 1.46 | 1.36 |

Note:
% exposure ratio = ketamine % parameter PO/ketamine % parameter IN
For AUC, $AUC_{0-4\,hr}$ and $AUC_{0-1\,hr}$ were used for PO and IN, respectively($AUC_{0-0.5\,h}$ for IN KTM-CO$_2$CH$_2$-nicotinoyl-Gln).

The pharmacokinetics ketamine (Table 13) and norketamine (Table 14) in plasmas after intravenous administration in rats were also assessed. The blood samples were taken at 0.0833, 0.25, 0.5, 1, 2, and 3 hours post-dose, and each dose was the molar equivalent to 2.32 mg/kg Ketamine HCl.

TABLE 13

Mean Pharmacokinetic Parameters of Ketamine in Plasma after Intravenous Administration in Sprague-Dawley Rats.

| | Analyte = Ketamine | | |
|---|---|---|---|
| Conjugate | $C_{max}$ (ng/mL) | $AUC_{0-3\,hr}$ (h*ng/mL) | $T_{max}$ (hours) |
| KTM-CO$_2$CH$_2$-nicotinoyl-Pro 10f | 170 | 202 | 0.50 |
| KTM-CO$_2$CH$_2$-nicotinoyl-Gln 10k[a] | 213 | 284 | 0.50 |

'TABLE 14

Mean Pharmacokinetic Parameters of Norketamine in Plasma after Intravenous Administration in Sprague-Dawley Rats.

| | Analyte = Ketamine | | |
|---|---|---|---|
| Conjugate | $C_{max}$ (ng/mL) | $AUC_{0-3\,hr}$ (h*ng/mL) | $T_{max}$ (hours) |
| KTM-CO$_2$CH$_2$-nicotinoyl-Pro 10f | 80.7 | 133 | 1.00 |
| KTM-CO$_2$CH$_2$-nicotinoyl-Gln 10k[a] | 40.2 | 85.4 | 1.00 |

The pharmacokinetic data from these studies were used to also assess the relative intravenous bioavailability of ketamine (Table 15) and norketamine (Table 16) of the ketamine compounds as compared to ketamine HCl in Sprague-Dawley rats. The calculated % parameter (i.e., % $C_{max}$ or % AUC) is equal to the mean conjugate PK parameter/mean comparator PK parameter.

TABLE 15

Relative Intravenous Bioavailability of Ketamine vs Study Comparator (Ketamine HCl) in Sprague-Dawley Rats.

| | Analyte = Ketamine | |
|---|---|---|
| Conjugate | % $C_{max}$ | % $AUC_{0-3\ hr}$ |
| KTM-CO$_2$CH$_2$-nicotinoyl-Pro 10f | 91.0% | 129% |
| KTM-CO$_2$CH$_2$-nicotinoyl-Gln 10k$^a$ | 76.2% | 175% |

Note:
% parameter = mean conjugate parameter/mean comparator parameter

TABLE 16

Relative Intravenous Bioavailability of Norketamine vs Study Comparator (Ketamine HCl) in Sprague-Dawley Rats.

| | Analyte = Ketamine | |
|---|---|---|
| Conjugate | % $C_{max}$ | % $AUC_{0-3\ hr}$ |
| KTM-CO$_2$CH$_2$-nicotinoyl-Pro 10f | 96.9% | 75.2% |
| KTM-CO$_2$CH$_2$-nicotinoyl-Gln 10k$^a$ | 35.9% | 43.5% |

Note:
% parameter = mean conjugate parameter/mean comparator parameter

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

It will be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The presently described technology is now described in such full, clear, concise, and exact terms as to enable any person skilled in the art to which it pertains to practice the same. It is to be understood that the foregoing describes preferred aspects of the invention and that modifications may be made therein without departing from the spirit or scope of the invention.

What is claimed is:

1. A compound having a structure of Formula III, or a pharmaceutically acceptable salt thereof:

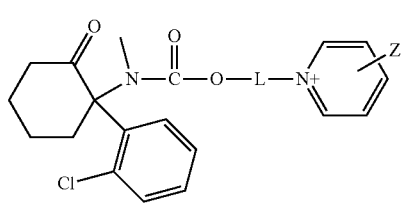

Formula III wherein L is alkyl;
wherein Z is selected from hydrogen,

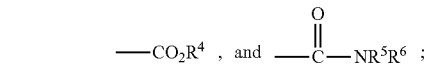

and wherein $R^4$, $R^5$, and $R^6$ are independently selected from hydrogen, alkyl, alkenyl, alkynyl, alkoxy, alkylamino, aryl, substituted aryl, and cycloalkyl.

2. A compound having a structure of Formula IV, or a pharmaceutically acceptable salt thereof:

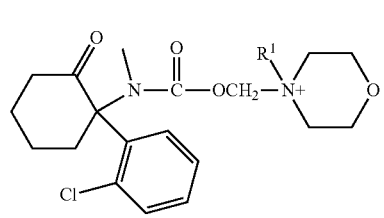

Formula IV wherein $R^1$ is selected from hydrogen, alkyl, alkenyl, alkynyl, alkoxy, alkylamino, aryl, substituted aryl, and cycloalkyl.

3. The compound of claim 1 having a structure selected from the group consisting of:

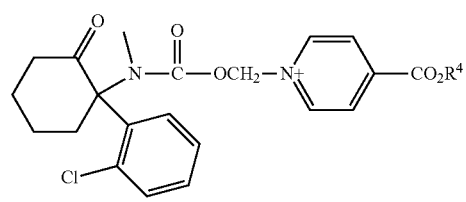

wherein $R^4$ is tert-butyl or hydrogen.

4. The compound of claim 1 having a structure selected from the group consisting of:

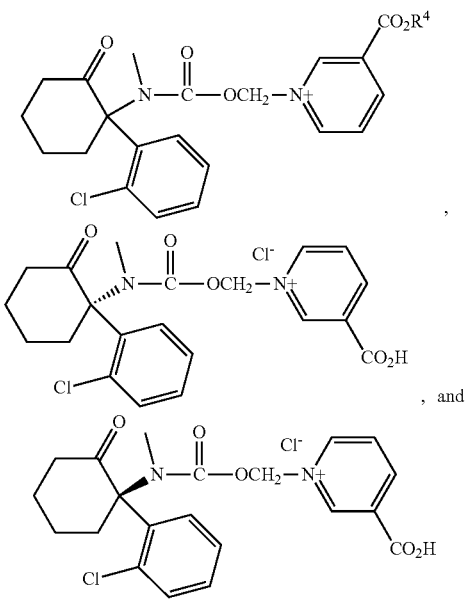

wherein $R^4$ is tert-butyl, methyl, ethyl, or hydrogen.

5. The compound of claim 1 having a structure selected from the group consisting of:
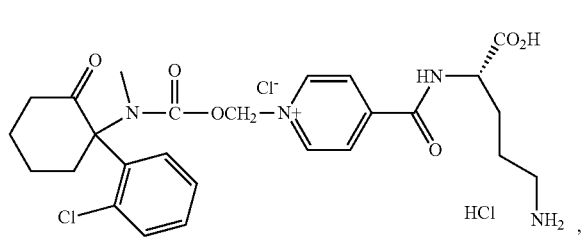
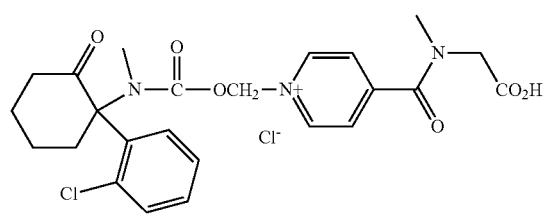
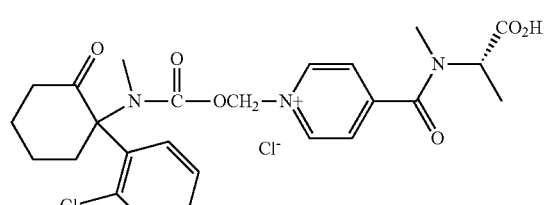
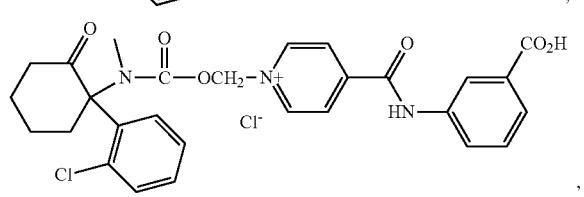
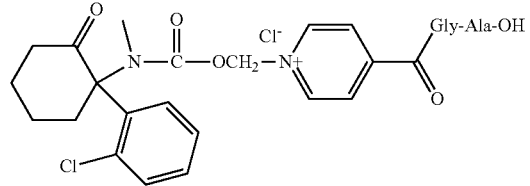
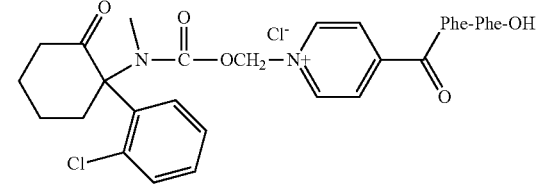
6. The compound of claim 1 having a structure selected from the group consisting of:
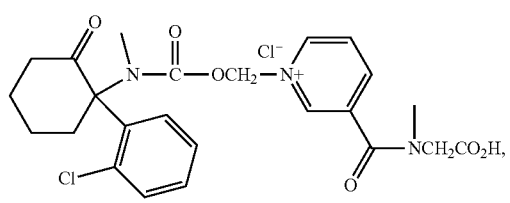
-continued
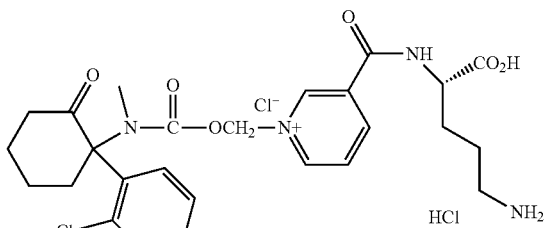
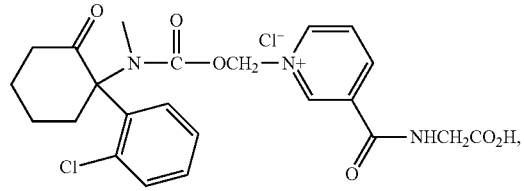
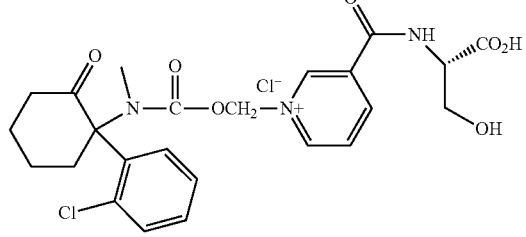
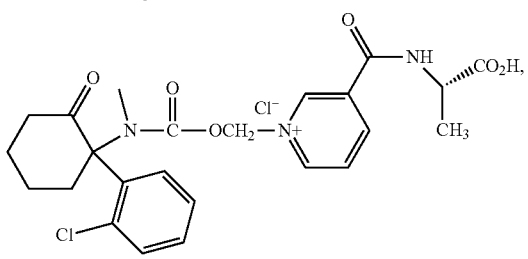
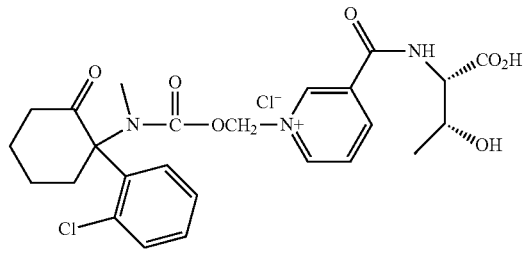
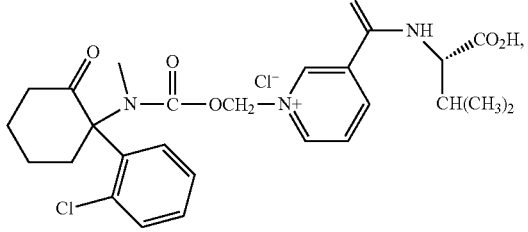
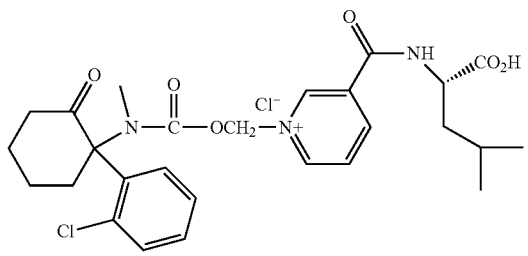

-continued

-continued
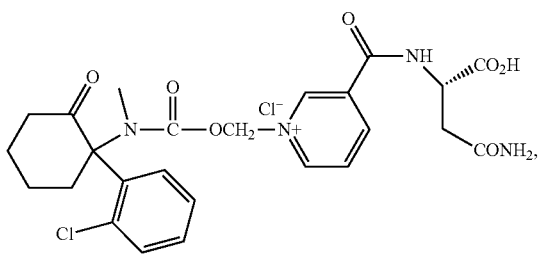
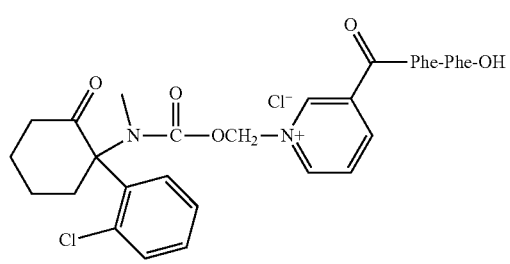
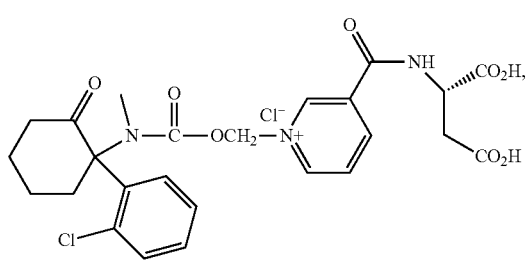
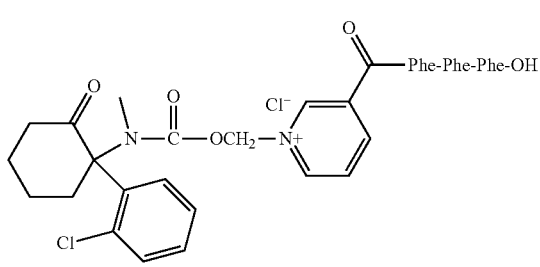
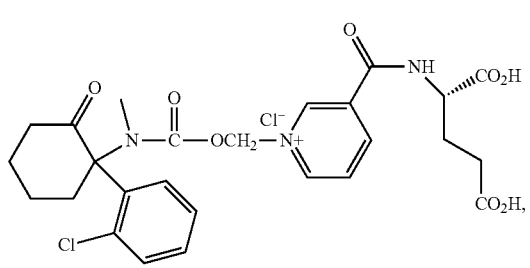
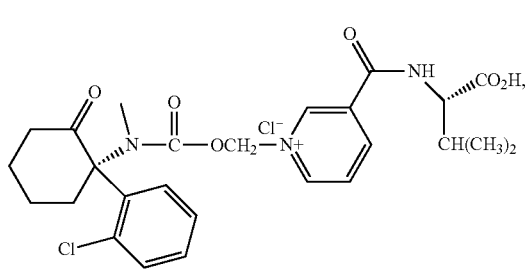
-continued
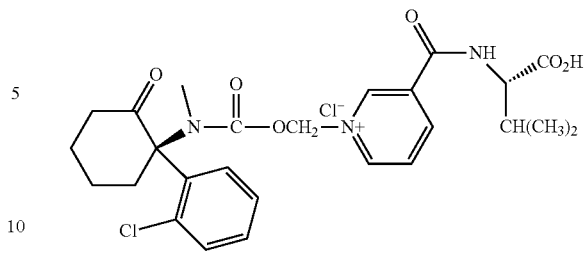
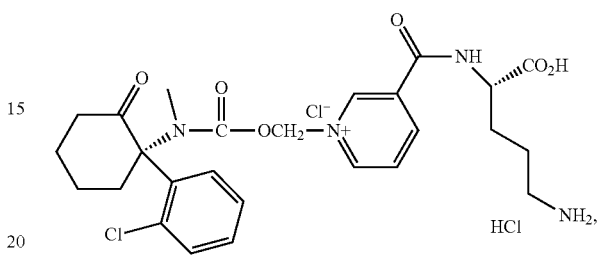
and
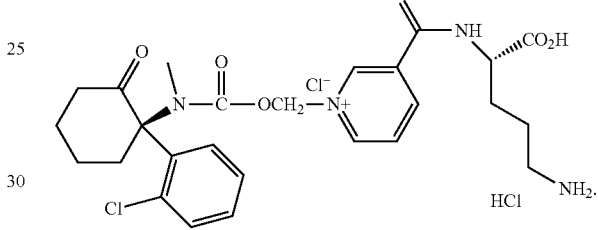
7. The compound of claim 1 having a structure selected from the group consisting of:
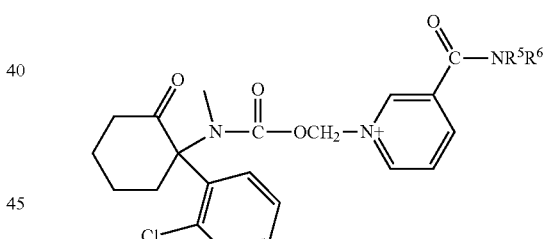
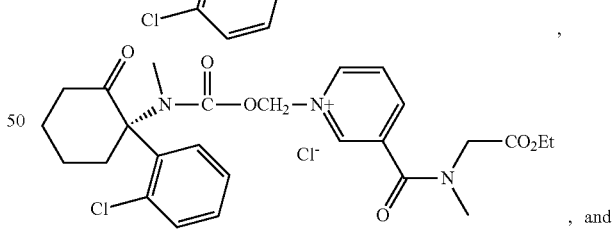
, and
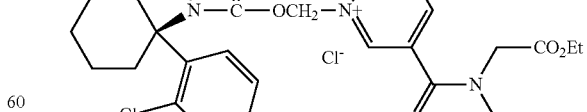
wherein $NR^5R^6$ is $NH_2$, $NHCH_2CO_2CH_2CH_3$, $NCH_3(CH_3)$, $NCH_3(OCH_3)$, $NCH_3(OCH_2C_6H_5)$, $NCH_3(CH_2CO_2CH_2CH_3)$, morpholine, or methyl pipecolinate.

8. The compound of claim 1 having a structures selected from the group consisting of:

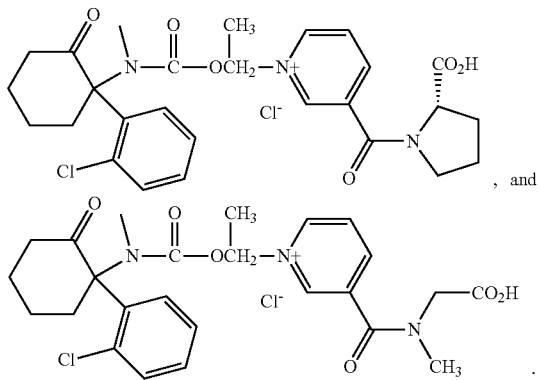

, and

9. The compound of claim 2 having the following structure:

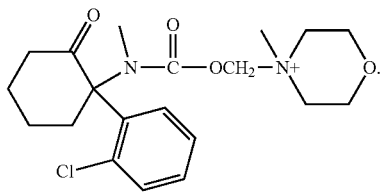

10. A compound having a structure selected from the group consisting of:

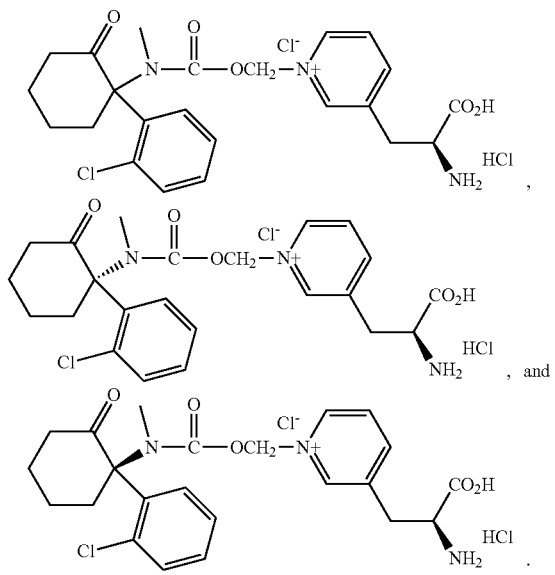

11. The compound of any one of claims 1-2, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

12. A composition comprising the compound of any one of claims 1-2, 3-9 or 10, or a pharmaceutically acceptable salt of the compound.

13. The composition of claim 12, wherein the composition further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

14. The composition of claim 12 or claim 13, wherein the composition is in a form selected from the group consisting of a liquid, a sublingual, a gummy, a chewable tablet, a rapidly dissolving tablet, a tablet, a capsule, a caplet, a troche, a lozenge, an oral powder, a solution, a thin strip, an oral thin film (OTF), an oral strip, a rectal film, a syrup, a suspension, or a suppository.

15. The composition of any one of claims 12-14, wherein the composition has a dosing regimen that is about two times a day or less.

16. The composition of any one of claims 12-14, wherein the composition has a dosing regimen that is about one time a day.

17. The composition of any one of claims 12-16, wherein the composition is administered orally, intranasally, or intravenously to a subject in need thereof.

18. The composition of claim 17, wherein the subject is a human or animal subject.

19. The composition of any one of claims 12-18, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

20. An oral formulation comprising a therapeutically effective dose of a compound of any one of claims 1-2, 3-9 or 10, or a pharmaceutically acceptable salt of the compound.

21. The oral formulation of claim 19, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, mesotartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

22. The oral formulation of claim 20 or claim 21, wherein oral formulation is in the form selected from the group consisting of a liquid, a sublingual, a gummy, a chewable tablet, a rapidly dissolving tablet, a tablet, a capsule, a caplet, a troche, a lozenge, an oral powder, a solution, a thin strip, an oral thin film (OTF), an oral strip, a syrup, or a suspension.

23. The oral formulation of any one of claims 20-22, wherein the oral formulation has a dosing regimen that is about two times a day or less.

24. The oral formulation of any one of claims 20-22, wherein the oral formulation has a dosing regimen that is about one time a day.

25. A pharmaceutical kit comprising:
a specified amount of individual doses in a package, wherein each individual dose comprises a therapeutically effective amount of a composition comprising a compound of any one of claims 1-2, 3-9 or 10, or a pharmaceutically acceptable salt of the compound.

26. The pharmaceutical kit of claim 25, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, mesotartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

27. A method for increasing oral bioavailability, reducing norketamine exposure, reducing intranasal bioavailability, reducing intravenous bioavailability, and/or providing an extended or delayed release of ketamine as compared to ketamine exposure and/or administration, the method comprising administering to a subject in need thereof a compound of any one of claims 1-2, 3-9 and 10, a pharmaceutically acceptable salt of the compound, or a composition of any one of claims 12-18, an oral formulation of any one of claims 19-23, or a pharmaceutical kit of claim 25 or claim 26.

28. The composition of any one of claims 12-14, wherein the composition provides reduced maximal exposure ($C_{max}$) and/or reduced total exposure (AUC) to ketamine when administered intranasally at an equimolar dose to unconjugated ketamine.

29. The composition of any one of claims 12-14, wherein the composition provides reduced maximal exposure ($C_{max}$) and/or reduced total exposure (AUC) to ketamine when administered intravenously at an equimolar dose to unconjugated ketamine.

30. The composition of any one of claims 12-14, wherein the composition provides reduced abuse potential or is resistant to abuse when administered intranasally and/or intravenously at an equimolar dose to unconjugated ketamine.

31. The composition of any one of claims 12-14, wherein the composition provides reduced maximal exposure ($C_{max}$) and/or reduced total exposure (AUC) to norketamine when administered orally at an equimolar dose to unconjugated ketamine.

32. The composition of any one of claims 12-14, wherein the composition provides reduced maximal exposure ($C_{max}$) and/or reduced total exposure (AUC) to norketamine when administered orally at a dose that provides therapeutically equivalent exposure to ketamine when compared to unconjugated ketamine.

33. The composition of any one of claims 12-14, wherein the composition provides an extended-release or delayed-release (longer $T_{max}$) of ketamine after oral administration when compared to a therapeutically equivalent oral dose of unconjugated ketamine.

\* \* \* \* \*